United States Patent [19]
Lewis et al.

[11] Patent Number: 6,040,186
[45] Date of Patent: *Mar. 21, 2000

[54] VIAL AUTOSAMPLER WITH SELECTABLE MODULES

[75] Inventors: Edmund T. Lewis, West Chester; Thomas B. Green, Batavia, both of Ohio

[73] Assignee: Tekmar Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/842,317

[22] Filed: Apr. 24, 1997

Related U.S. Application Data

[62] Division of application No. 08/735,485, Oct. 23, 1996, which is a continuation of application No. 08/273,537, Jul. 11, 1994, abandoned.

[51] Int. Cl.[7] .................................................... G01N 35/10
[52] U.S. Cl. ................................ 436/53; 436/52; 436/54; 436/161; 436/174; 436/179; 436/180; 422/70; 422/81; 422/82; 422/89; 422/100; 422/103
[58] Field of Search ................................ 422/63, 65, 70, 422/89, 100, 101, 102, 103, 104, 81, 82; 436/43, 49, 54, 161, 174, 52, 180, 53, 179

[56] References Cited

U.S. PATENT DOCUMENTS

| | | | |
|---|---|---|---|
| 2,541,272 | 2/1951 | Murphy | 226/19 |
| 3,912,456 | 10/1975 | Young | 23/253 R |

(List continued on next page.)

FOREIGN PATENT DOCUMENTS

| | | |
|---|---|---|
| 0 635 713 A1 | 1/1995 | European Pat. Off. . |
| 60-42959 | 3/1985 | Japan . |
| 60-79135 | 6/1985 | Japan . |
| 62-162647 | 10/1987 | Japan . |
| 59-192957 | 11/1994 | Japan . |
| WO 91/13350 | 9/1991 | WIPO . |
| WO 92/05448 | 4/1992 | WIPO . |
| WO 92/15 875 | 9/1992 | WIPO . |

OTHER PUBLICATIONS

O.I. Corporation Model 4460A Sample Concentrator Manual table of contents page and pp. 9, 61–64, and pp. 85–101 (admitted prior art—published at least as early as Jul. 1, 1993).

Article by M. Markelov et al. entitled "Automation of Multiple Analytical Procedures in an Industrial Laboratory . . . ", from *Advances in Laboratory Automation Robotics 1985*, pp. 209–230.

(List continued on next page.)

*Primary Examiner*—Long V. Le
*Attorney, Agent, or Firm*—Westman, Champlin & Kelly, P.A.

[57] ABSTRACT

A modular vial autosampler has a storage area for vials containing samples to be analyzed and at least one modular sampling station. A vial transfer mechanism lifts a sample vial from the storage section, moves it to a station for identification and then to a sampling station, and under central control activates the sampling station for obtaining a sample for analysis. The vial transfer mechanism is movable in x, y, and z directions to capture and move a selected vial. The autosampler has a series of valves operable under central control to selectively introduce two different standards into the sample, and after obtaining the sample, for rinsing and purging the conduits or lines and needles to reduce sample carryover. The modular vial autosampler includes controls to selectively sample either a gas or a liquid using many of the same components.

3 Claims, 16 Drawing Sheets

U.S. PATENT DOCUMENTS

| | | |
|---|---|---|
| 4,070,284 | 1/1978 | Fujita et al. .............................. 210/31 |
| 4,094,197 | 6/1978 | Harris, Sr. et al. . |
| 4,095,472 | 6/1978 | Mowery, Jr. ..................... 73/422 GC |
| 4,112,743 | 9/1978 | Mowery, Jr. ....................... 73/61.1 C |
| 4,200,607 | 4/1980 | Suzuki ..................................... 422/64 |
| 4,279,860 | 7/1981 | Smolen .................................... 422/63 |
| 4,313,735 | 2/1982 | Yamashita et al. ...................... 23/230 |
| 4,342,341 | 8/1982 | Lee .......................................... 141/1 |
| 4,359,891 | 11/1982 | Ahlstrom, Jr. et al. ................ 73/23.1 |
| 4,476,733 | 10/1984 | Chlosta et al. ....................... 73/863.91 |
| 4,478,095 | 10/1984 | Bradley et al. ...................... 73/864.21 |
| 4,520,108 | 5/1985 | Yoshida et al. .......................... 436/52 |
| 4,532,969 | 8/1985 | Kwaan .................................... 141/27 |
| 4,536,199 | 8/1985 | Toon ....................................... 422/89 |
| 4,558,603 | 12/1985 | Chlosta et al. ...................... 73/864.21 |
| 4,578,244 | 3/1986 | Cosgrove, Jr. et al. .................. 422/65 |
| 4,622,457 | 11/1986 | Bradley et al. ......................... 235/464 |
| 4,680,270 | 7/1987 | Mitsumaki et al. ..................... 436/52 |
| 4,699,718 | 10/1987 | Jones et al. ............................. 210/659 |
| 4,710,355 | 12/1987 | Ushikubo ............................... 422/100 |
| 4,713,974 | 12/1987 | Stone .................................. 73/864.23 |
| 4,754,657 | 7/1988 | Schneider ................................ 73/866 |
| 4,890,930 | 1/1990 | Nohso ................................... 366/208 |
| 4,920,056 | 4/1990 | Dasgupta ................................ 436/50 |
| 4,924,716 | 5/1990 | Schneider ................................ 73/866 |
| 4,944,781 | 7/1990 | Ruggirello et al. ...................... 55/386 |
| 4,969,993 | 11/1990 | Nash, Jr. et al. .................... 210/198.2 |
| 5,012,845 | 5/1991 | Averette ................................. 141/329 |
| 5,042,293 | 8/1991 | Heyde ................................ 73/61.1 C |
| 5,080,864 | 1/1992 | Shaw ....................................... 422/62 |
| 5,094,961 | 3/1992 | del Valle et al. ....................... 436/180 |
| 5,096,670 | 3/1992 | Harris et al. ............................. 422/65 |
| 5,100,557 | 3/1992 | Nogami et al. ......................... 210/656 |
| 5,108,705 | 4/1992 | Rounbehler et al. ..................... 422/89 |
| 5,147,551 | 9/1992 | Averette ................................. 210/640 |
| 5,152,176 | 10/1992 | Bryselbout et al. ................... 73/23.41 |
| 5,158,748 | 10/1992 | Obi et al. ................................ 422/100 |
| 5,158,895 | 10/1992 | Ashihara et al. ....................... 436/526 |
| 5,254,311 | 10/1993 | Kubo ....................................... 422/81 |
| 5,260,028 | 11/1993 | Astle ....................................... 422/81 |
| 5,262,049 | 11/1993 | Ferkany .................................. 210/258 |
| 5,277,871 | 1/1994 | Fujii et al. ................................ 422/70 |
| 5,308,583 | 5/1994 | Sanuki ................................... 422/100 |
| 5,316,954 | 5/1994 | Hupe et al. ............................... 436/89 |
| 5,380,486 | 1/1995 | Anami ..................................... 422/63 |
| 5,384,093 | 1/1995 | Ootani et al. ............................ 422/63 |
| 5,393,434 | 2/1995 | Hutchins et al. ....................... 210/656 |
| 5,403,386 | 4/1995 | Collier et al. ............................ 96/105 |
| 5,417,922 | 5/1995 | Markin et al. ........................... 422/65 |
| 5,424,037 | 6/1995 | Zimmerman et al. .................. 422/104 |
| 5,427,743 | 6/1995 | Markin ................................... 422/104 |
| 5,432,098 | 7/1995 | Wilks ..................................... 436/178 |
| 5,436,166 | 7/1995 | Ito et al. ................................. 436/161 |
| 5,455,006 | 10/1995 | Aota et al. ............................... 422/63 |
| 5,462,660 | 10/1995 | Singleton et al. .................... 210/198.2 |
| 5,468,643 | 11/1995 | Su et al. ................................. 436/161 |
| 5,472,669 | 12/1995 | Miki et al. ............................... 422/63 |
| 5,483,843 | 1/1996 | Miller et al. ......................... 73/864.23 |
| 5,525,298 | 6/1996 | Anami ..................................... 422/63 |
| 5,578,495 | 11/1996 | Wilks ..................................... 436/178 |

OTHER PUBLICATIONS

Article by M. Markelov et al. entitled "Analysis of Water and Soils for Trace Organic Contamination via Headspace and Purge and Trap Techniques Using Robots", from the proceedings of the Tenth Annual Symposium of the U.S. Environmental protection Agency Office of Water (May 13–4, 1987) pp. 248–266.

Article by F. Jones entitlted "Automatic Samplers for Gas Chromatography" from J. Chromatographic Science (Dec. 1980) pp. 664–669.

A brochure from Dynatech Precision Sampling Corp. entitlted "Introducing DynaWaters", dated Feb. 1992.

Five one–page sheets from Dynatech Precision Sampling Corp. entitlted "PTA–30", "PTA–30W/S", "Dynasoils", "Dynawaters", and "Dyatrap" (all undated).

A brochure from Dynatech Precision Sampling Corp. entitlted "Introducing DynaSoils", dated Jul. 30, 1993.

A brochure from Dynatech Precision Sampling Copr. entitlted "PTA–30W/S Autosampler", dated Jul. 1993.

Operating manual for "PTA–30", dated May 1988.

Operating manual for "PTA–30W/S", dated May 1990.

A brochure by Tekmar Company entitlted "Concentrating on Tomorrow's Chromatography Today" (undated).

A brochure by Tekmar Company entitlted "2000 Series Concentrator Systems . . . " (undated).

Selected pages from "Catalog 94–95" Tekmar (undated).

Tekmar TekNOTE, "Glassware Options for Purge & Trap Concentrators", by J. Twachtman and E. Heggs, Winter 1994, vol. 3.3, pp. 1–3.

"Theory of Purge and Trap Gas Chromatography Purge Efficiency" pp. 3–5, publication date believed to be 1 year prior to effective date of filing of this application.

Aquatek 50 User Manual—Tekmar Company, pp. 1–5; 3–5 through 3–9; 4–7 through 4–13; 5–25 through 5–36, drawings of Aquatek 50 namely right interior; right top interior components and lower left interior components; and Aquatek 50 flow diagrams for prepurge; sample pressure #1 or #2; empty vial; and backflush needle. Published May 6, 1994. (admitted prior art).

Set of drawings of needle for Aquatek 50 labeled Aquatek 1 through Aquatek 5, illustrating public use structure as of May 6, 1994. (admitted prior art).

ALS 2016/ALS 2032 User Manual—Tekmar Company, pages bearing ALS2016 front view and upper right view; pp. 21, 22, 54, 55, 66, 67, 68 and pages bearing sample heater positioning diagram; ¾ Glassware Diagram and Drawings No. 14–3236–000 and flow diagram, publication revised Jan. 31, 1994. (admitted prior art).

Drawing labeled 2016–1 showing needle; believed publically available at least as early as Jan. 31, 1994. (admitted prior art).

Three drawings 7000–1; 7000–2 and 7000–3 showing needle in PCT Publication WO 91/13350—in public use at least by Sep. 5, 1991.

"Automatic Methods of Analysis "by, Valcárcel et al., Techniques and Instrumentation in Analytical Chemistry, vol. 9, 1988.

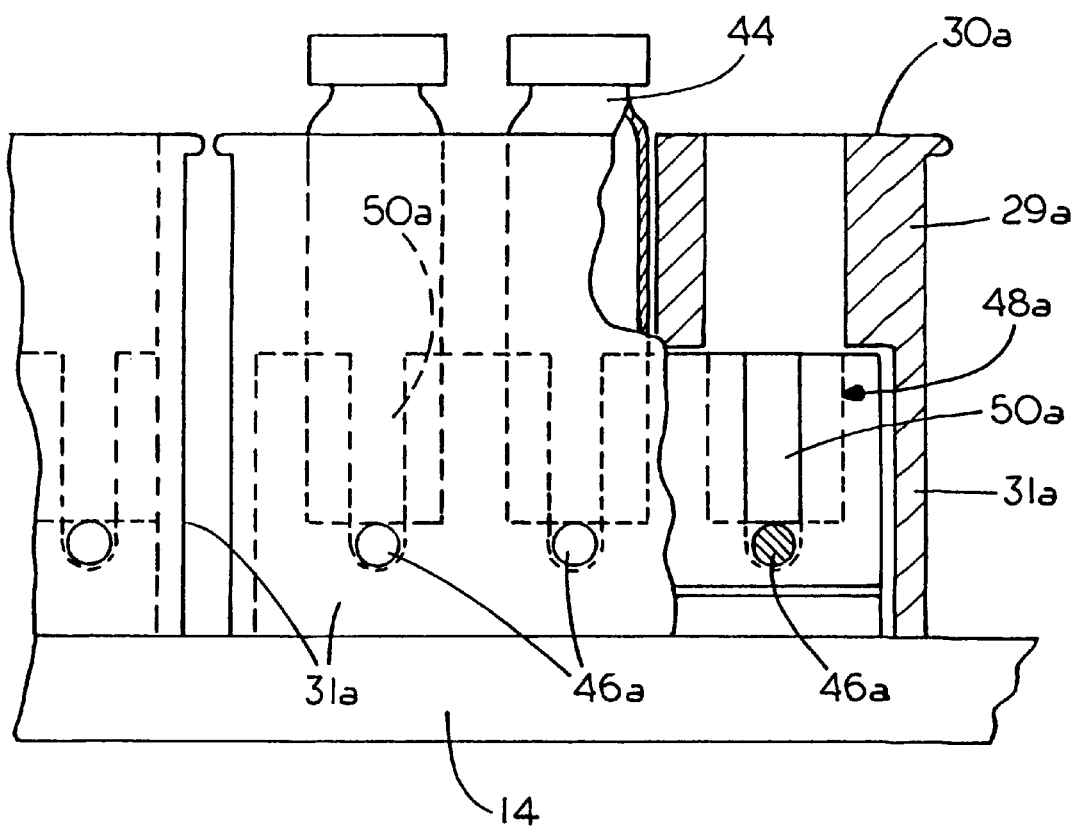

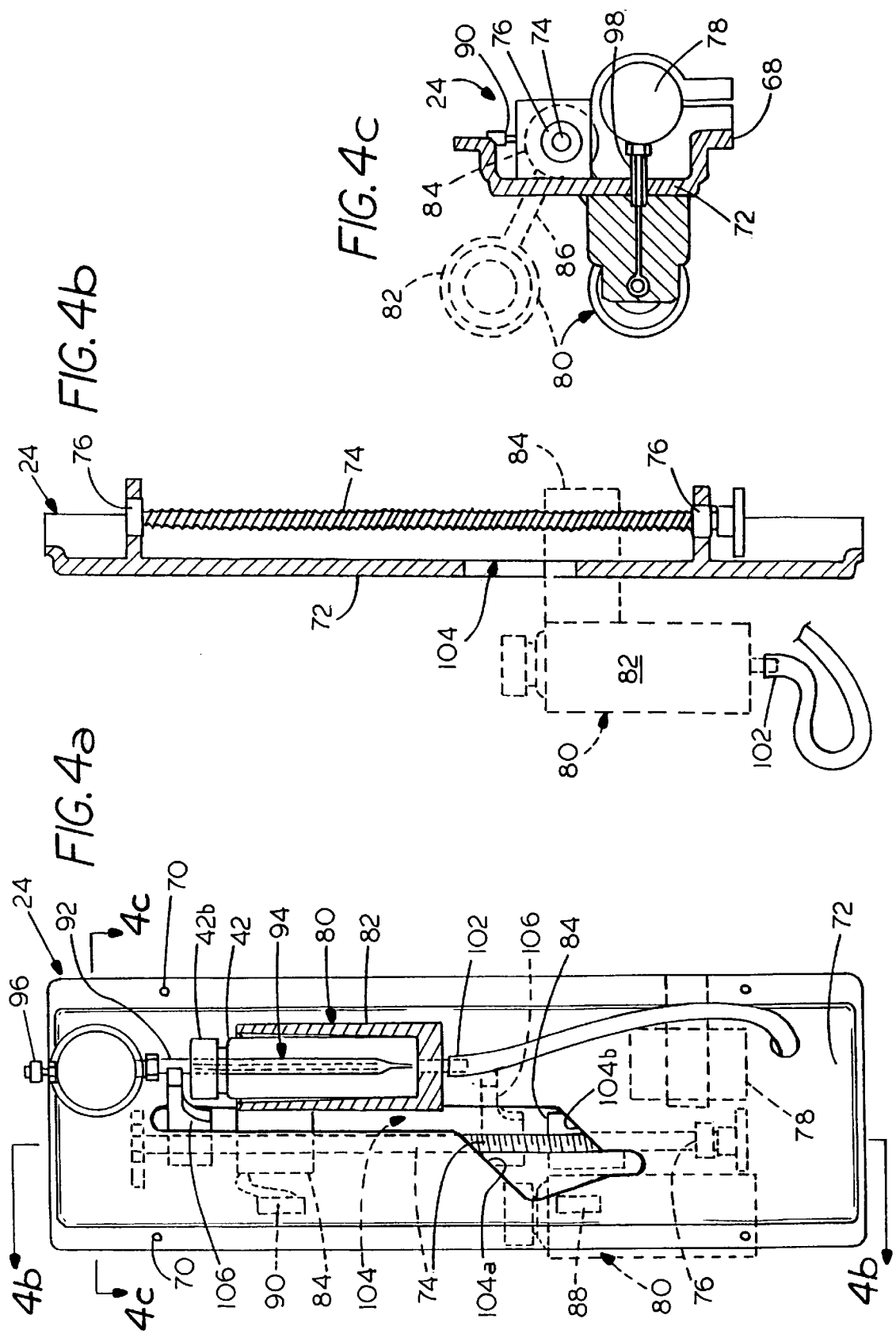

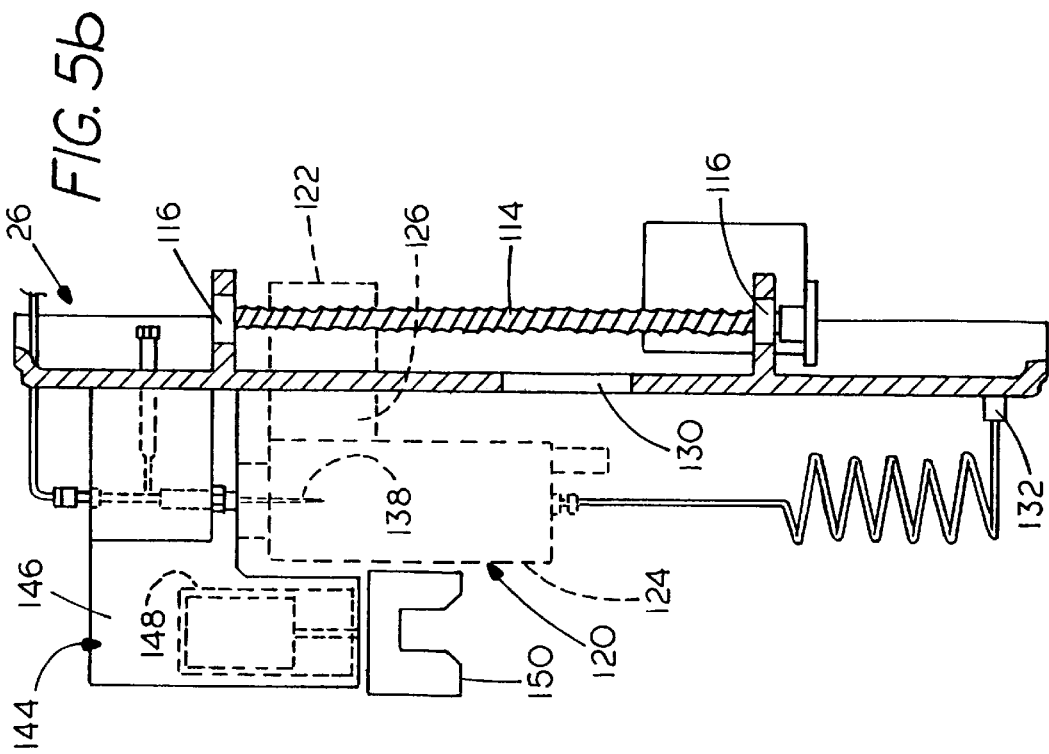
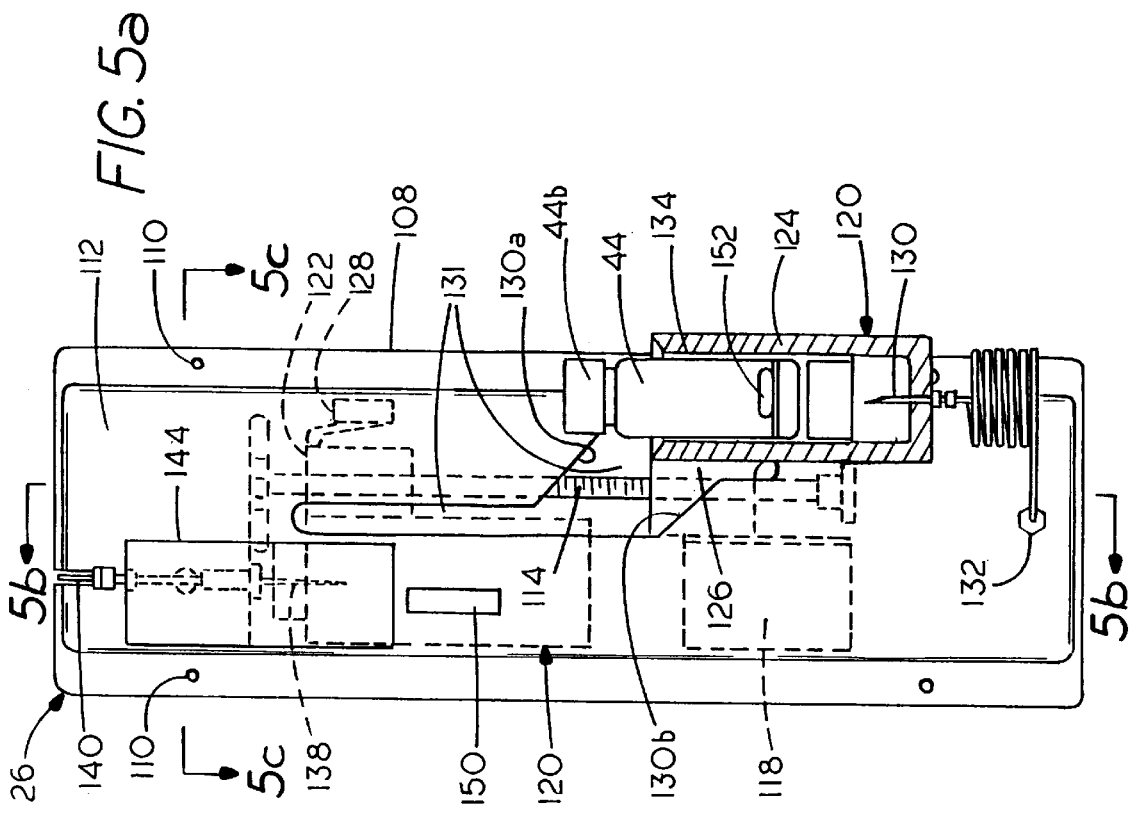

VIAL AUTOSAMPLER WITH SELECTABLE MODULES

This is a divisional of application Ser. No. 08/735,485, filed Oct. 23, 1996, which is a continuation of Ser. No. 08/273,537, filed Jul. 11, 1994 abandoned.

BACKGROUND OF THE INVENTION

The present invention relates to machines that accept chemical specimens or samples and extract fluid containing volatile components from the chemical samples for later analysis. More particularly, the invention relates to machines that accept vials that carry such specimens, which machines convey the fluid or at least the volatiles therein to a chemical species analyzer such as a gas chromatograph.

Gas chromatographs and similar chemical species analyzers such as mass spectrometers are known. Vial handling machines, such as the model 7000 Headspace Autosampler sold by Tekmar Co., Cincinnati, Ohio, USA, are also known. The model 7000 extracts from a covered vial a predetermined amount of fluid from a static gaseous headspace above a sample, and conveys the predetermined amount of fluid (containing volatiles to be identified) to a gas chromatograph. Vial autosamplers using dynamic headspace techniques are also known, such as the model PTA-30W/S Autosampler sold by Dynatech Precision Sampling Corp., Baton Rouge, La., USA. The model PTA-30W/S routes a purge gas into a covered vial containing a sample, and provides an outlet from the vial to carry the exiting fluid (comprising the purge gas and volatile components from the sample) to a separate concentrator trap unit. After the volatile components are collected on the trap, they are flushed into a gas chromatograph for analysis. The model PTA-30W/S can also extract a liquid sample containing volatiles from a covered vial and transfer it to a separate unit which sparges the liquid sample and traps the volatile components, for later transfer to a gas chromatograph.

SUMMARY OF THE INVENTION

In one aspect of the present invention, a vial handling device comprises a base unit and a sampling module adapted to mate with the base unit. The vial handling device extracts a fluid comprising volatile components from a vial which holds a specimen to be analyzed. The base unit has a vial storage area to hold multiple vials, and a sampling station where the fluid is removed from the vial. The sampling module has a needle assembly to penetrate the vial to remove the fluid, and mates with the base unit proximate the sampling station. In a preferred embodiment, the base unit has a second sampling station, and the vial handling device includes a second sampling module that mates with the base unit proximate the second sampling station.

In another aspect of the invention, a series of sequentially controlled valves, coupled with a syringe type pump provides for the analysis of samples removed from the vials, and includes a method of using one or two standards for inclusion with the specimen. The flowpaths also include a liquid flush for glassware and for flushing the needles.

In another aspect of the invention, a vial handling device moves a vial having a specimen therein from a loading site to a sampling site, and includes a carrier adapted to hold the vial, an elevator coupled to the carrier, and a mechanism to translate the carrier laterally as the vial is transported from the loading site to the sampling site.

In still another aspect of the invention, a vial handling device includes a base unit having a vial storage area, and a vial transporter. The vial transporter includes a main arm projecting from the base unit along a first axis, the main arm being adapted for translation along a second axis substantially perpendicular to the first axis. The vial transporter also includes a vial gripper assembly adapted for translation along the main arm, the vial gripper assembly including a gripper head adapted for translation along a third axis substantially perpendicular to the first and second axes.

In another aspect of the invention, an autosampler device includes a base unit having a port therein, a central control circuit including a removable circuit module disposed proximate the port, and a panel which is sized and movably held to the base unit to alternately cover and expose the port, thereby providing access to the removable circuit module through the port.

BRIEF DESCRIPTION OF THE DRAWINGS

FIG. 3a is a fragmentary end view of a vial holder assembly with parts broken away to show a thermal block;

FIGS. 4a–4c show a front, side sectional, and top sectional view respectively of a first sampling module in accordance with the invention;

FIGS. 5a–5c show a front, side sectional, and top sectional view respectively of a second sampling module in accordance with the invention;

FIG. 5d shows a closeup sectional view of a vial holder assembly in FIG. 5a;

FIG. 6b shows a sectional view along line 6b—6b in FIG. 6a;

For convenience, items in the figures having the same reference symbol are the same or serve the same or a similar function.

DETAILED DESCRIPTION OF THE PREFERRED EMBODIMENTS

Figure 1:
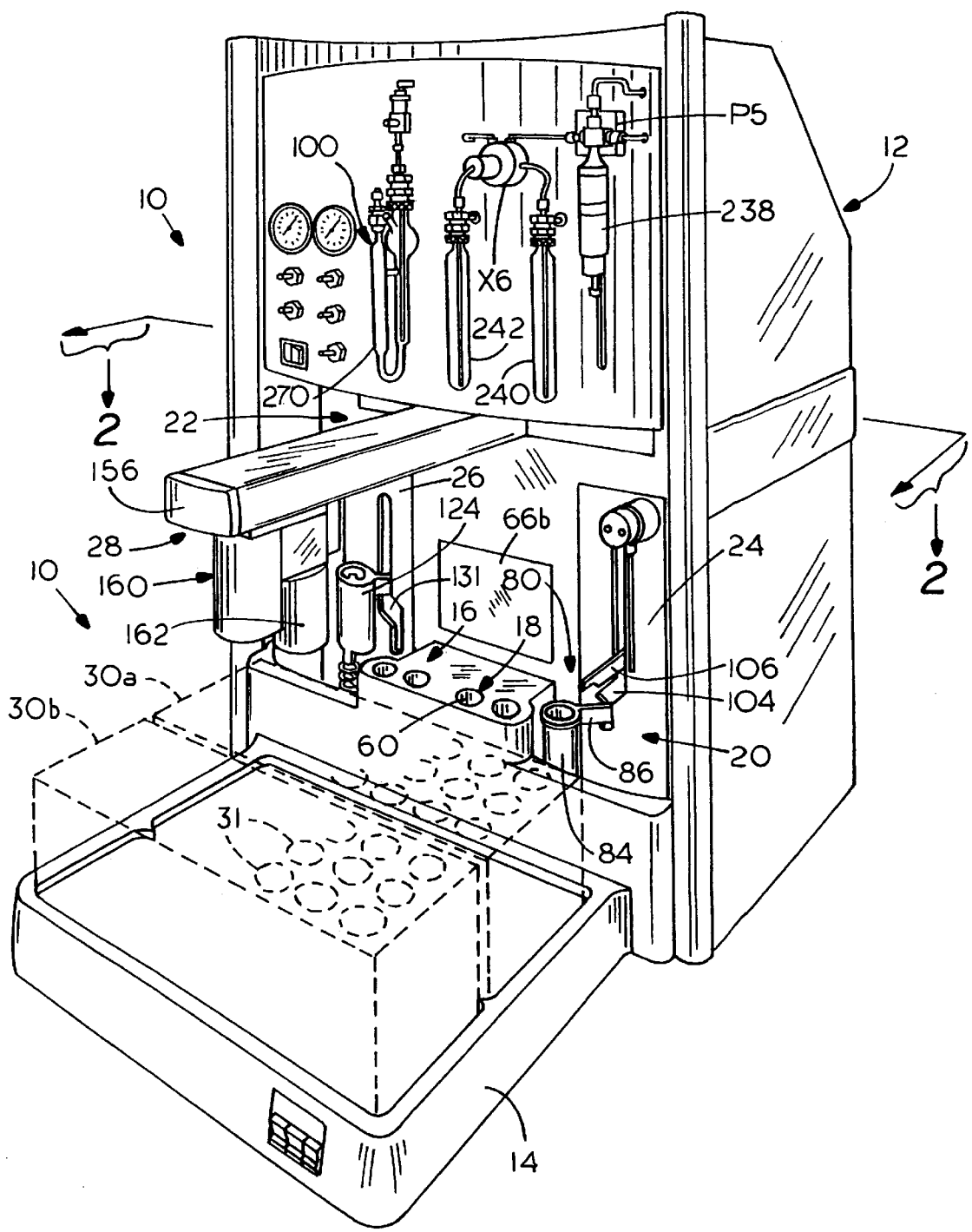
FIG. 1 is a perspective view of a vial autosampler device in accordance with the invention.

FIG. 1 shows a perspective view of a vial autosampler device 10 in accordance with the invention. The device 10 includes a base unit 12 that includes a vial storage platform area 14, a vial equilibration station 16, a vial identification station 18, separate first and second sampling stations 20 and 22, and a fluid handling system comprising valves, glasswork, and other fluid handling components. Device 10 also includes separate first and second sampling modules 24 and 26 each detachably mounted to the base unit 12 at sampling stations 20,22, respectively. Each sampling module 24 and 26 receives a vial containing a specimen and extracts a fluid from the vial for further analysis. Device 10 also includes a vial transporter 28 that carries individual vials between vial storage area 14, vial equilibration station 16, vial identification station 18, and the first and second sampling stations 20,22. Finally, device 10 includes a central programmable control circuit that accepts user inputs and controls the operation of device 10.

Figure 2:
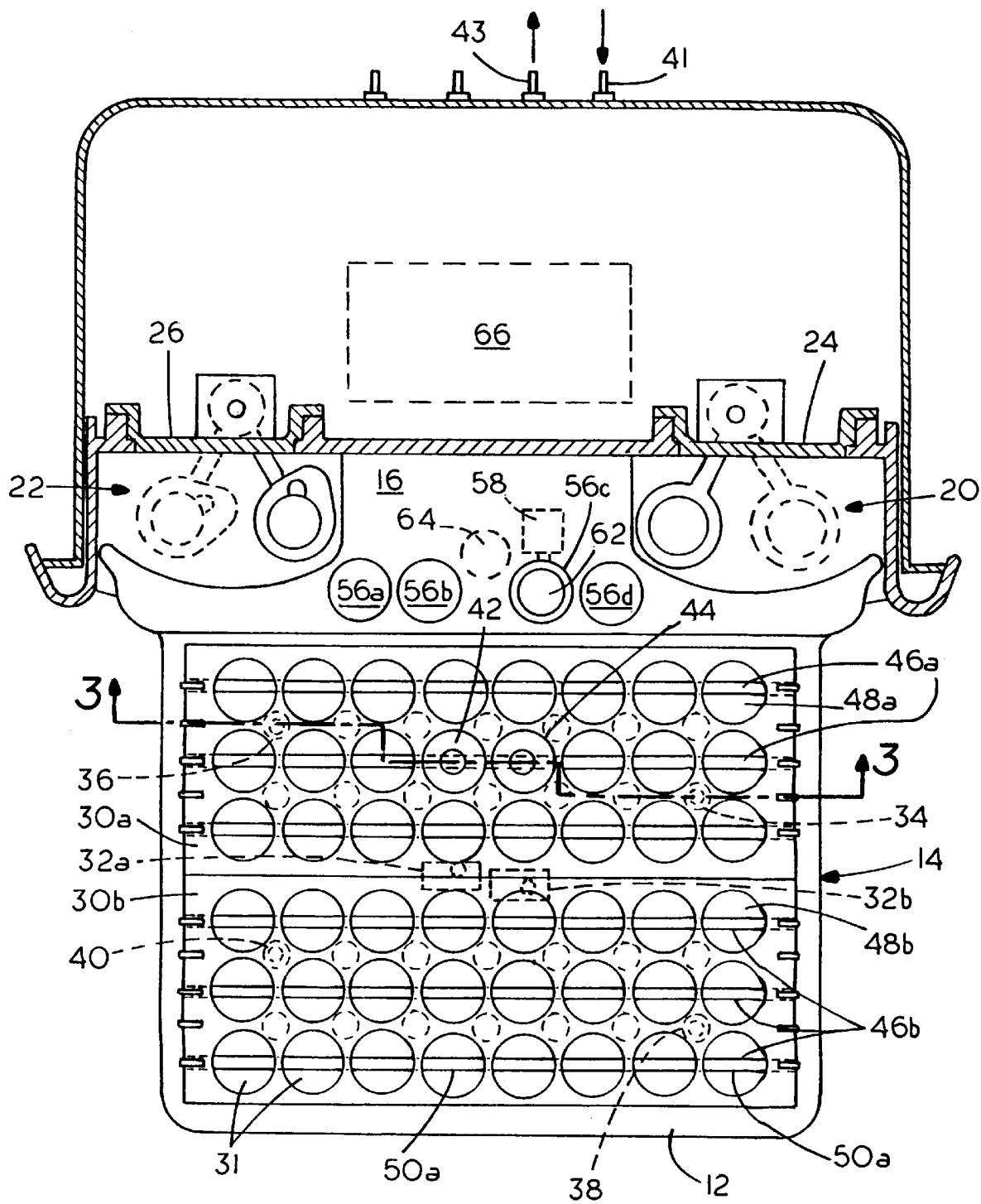
FIG. 2 is a cut-away view of the device of FIG. 1 along plane 2—2, with only key components shown and with some components shown in block form.

FIG. 2 shows a cutaway view of device 10 as taken along line 2—2 in FIG. 1. Vial storage area 14 includes a fixed or stationary platform shaped to receive removable vial racks 30a,30b, which vial racks are preferably substantially identical. Specimen-containing vials can be loaded into pockets or receptacles 31 of racks 30a,30b at a separate location and kept in storage until needed. The racks 30a, 30b each include upper portions 29a, 29b, and depending peripheral skirts 33a, 33b that support metal cross rods 46a, 46b. The rods 46a, 46b extend across the racks and are spaced below the upper portions 29a, 29b. The rods align with each pocket 31 and support the ends of vials placed in the pockets 31. When ready for testing, one or both of the loaded racks can be lowered into position at vial storage platform area 14. Included in vial storage platform area 14 are two push-button switches 32a,32b positioned on the platform to detect the presence of racks 30a,30b respectively. In each case, the weight of the loaded rack causes the rack skirt to depress the push-button to change the state of the switch.

Preferably, the skirts of racks 30a,30b slide down over thermal blocks 48a, 48b (one for each rack) which are fixedly mounted to vial storage platform area 14. The thermal blocks 48a have internal cavities or passageways 49 therein for fluid circulation. The cavities 49 are accessible from below the thermal blocks 48a, 48b by fittings 34,36, 38,40. (See FIGS. 2 and 3) Base unit 12 has an input fluid port 41 and a drain port 43 connected by internal tubing (not shown) to the fittings for a fluid circuit as follows as shown for thermal block 48a in FIG. 3: user-supplied fluid, such as tap water, enters port 41 and enters the cavity 49 of the thermal block underneath vial holder 30 a through fitting 34; the fluid drains via fitting 36 from that cavity and enters the cavity of the thermal block 48b underneath holder 30b through fitting 38; the fluid then exits the cavity via fitting 40 and leaves device 10 via drain port 43.

Figure 3:
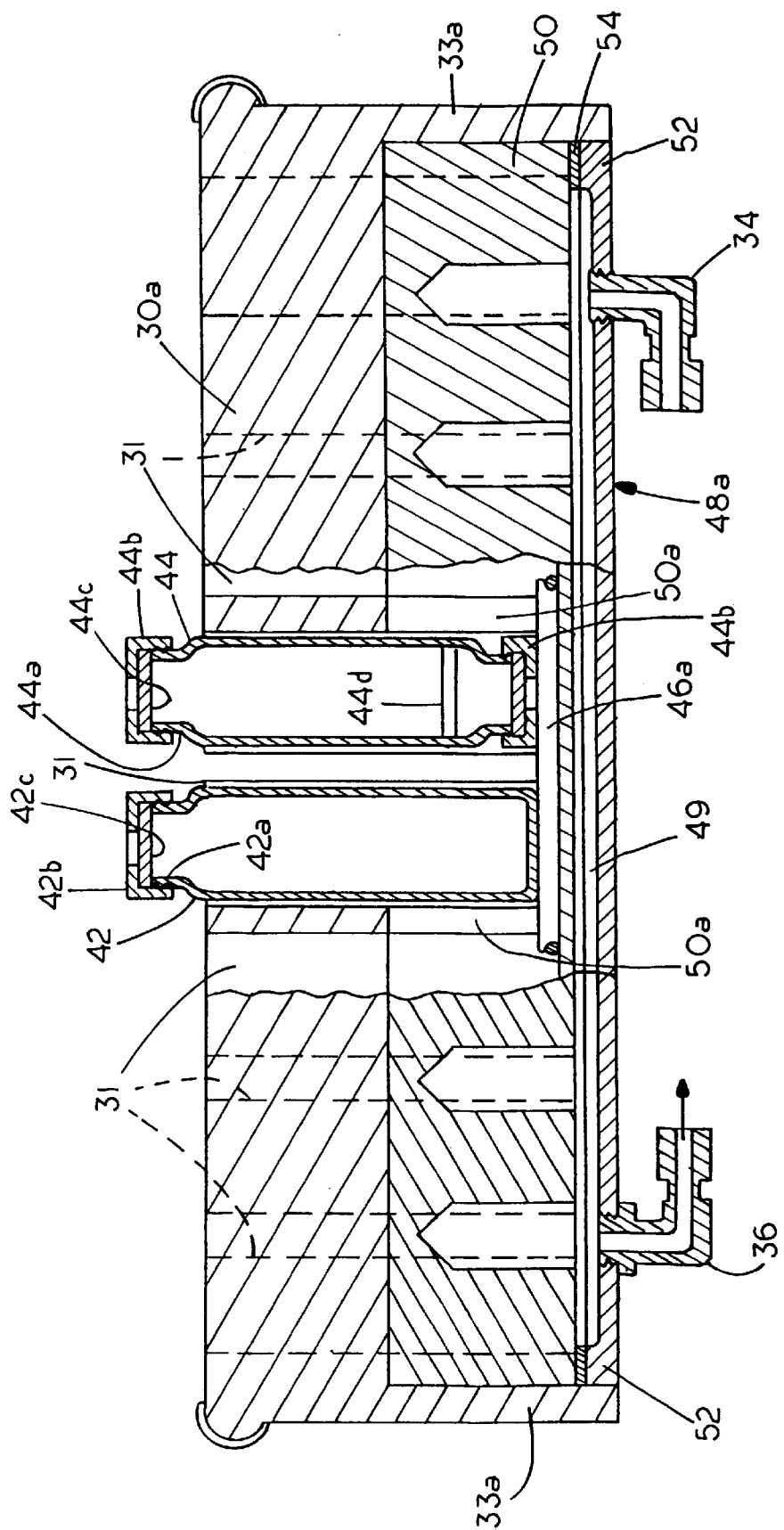
FIG. 3 is a sectional view along line 3—3 in FIG. 2.

Only a few of the vial receiving pockets or receptacles 31 of the rack/thermal block combination are shown occupied by specimen containing vials in FIGS. 2 and 3. Vial receiving pockets or receptacles 31 accept either a vial 42 having a single end cap 42b or a vial 44 having end caps 44b at each end. Vials 44 as shown in FIG. 3, preferably have a liquid retaining, gas porous divider frit 44d dividing each vial into upper and lower chambers. Each end cap can be crimped or, preferably, screwed onto the respective vial end. A septum 42c, 44c respectively, seals the specimen within the vial.

Each thermal block 48a, 48b includes a unitary upper portion 50, a lower portion 52, and a gasket 54 sandwiched therebetween. As shown typically, the internal fluid cavity 49 is formed between upper portion 50 and lower portion 52. Upper portion 50 is preferably composed of a high thermal conductivity material such as aluminum. The lower portion 52 is preferably composed of a low thermal conductivity material such as a suitable plastic to heat isolate the thermal blocks from the rest of base unit 12, thereby reducing thermal transfer to other parts of the base unit and reducing the time required to cool (or heat) the thermal blocks 48a, 48b. Base unit 12 remains at or near ambient temperature.

Channels 50a are cut in upper portion 50 of thermal blocks 48a, 48b to receive the metal rods 46a, 46b (FIG. 3a) so that when rack 30a, 30b rests in place at least the lower portion of each of the vials is substantially surrounded by and in thermal contact with the thermal blocks 48a, 48b. The metal rods 46a, 46b provide additional thermal conduction between the thermal block and the vials.

If desired, vial storage area 14 can comprise a vial-carrying rotating carousel or other known automated vial advancement device in place of the vial racks held stationary in storage area 14. The stationary vial racks allow high packing density of the vials over the entire vial storage area, thereby reducing the cross-sectional area ("footprint") of device 10 for a given number of vial storage positions. A small device footprint is an important consideration in many applications. Further, the use of stationary vial holders simplifies the construction and operation of device 10.

Turning again to FIG. 2, device 10 includes a vial equilibration area 16 comprising four ports 56a,56b,56c,56d in the base unit 12 where vials can be placed for a programmable period of time to warm up (or cool down) to the ambient room temperature. Port 56c also functions as vial identification station 18. An outer side wall of each vial has a sticker bearing a unique bar code pattern. An optical bar code reader assembly 58, available commercially and well known, is disposed in base unit 12 and views the side wall of the vial in port 56c through a vertical slot 60 (partially visible in FIG. 1) in the wall surrounding port 56c. A rotatable disk 62 is provided at the bottom of port 56c and is coupled to a stepper motor 64 controlled by a central control circuit 66. When stepper motor 64 rotates disk 62, the vial resting on the disk 62 rotates until the bar code pattern on the vial wall is detected by reader assembly 58 through slot 60. Central control circuit 66 then turns off stepper motor 64.

A vial can be transported by vial transporter 28 from the equilibration area 16 or directly from the vial storage area 14 to one of the sampling stations 20 or 22 where sampling operations are performed. At each of the sampling stations, a fluid is extracted from the vial. At sampling station 20, a liquid sample from a liquid specimen is extracted from the vial for subsequent sparging to remove volatiles from the liquid sample. At sampling station 22, a sample in the form of a gas or vapor is extracted from the vial during a sparging operation, after injecting a liquid into the vial to contact a liquid or solid (e.g. soil) specimen, stirring the resulting mixture, and heating the mixture.

According to one aspect of the invention, vial autosampler device 10 includes one or both sampling modules 24,26, which are adapted to mate with base unit 12 proximate sampling stations 20,22, respectively. Advantageously, vial autosampler device 10 can be outfitted with both or only one of the sampling modules, depending on the requirements of the user. If outfitted with only one module, the other module can be added to the device later.

Figure 10:
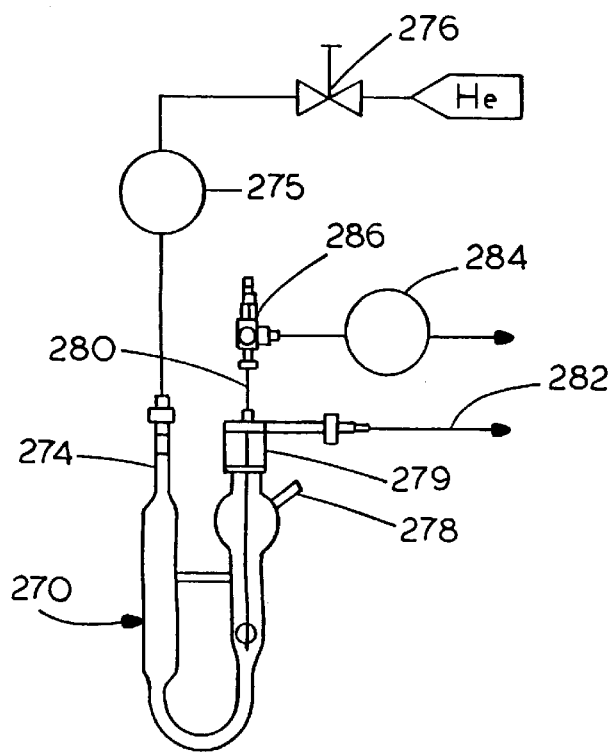
FIG. 10 is a view of a conventional sparging tube module includable in the vial autosampler of the present invention.

FIGS. 4a–4c show a front, side, and top view of sampling module 24. A plate 68 has mounting holes 70 for mounting by known means, such as screws, to base unit 12 such that a projecting face 72 of plate 68 mates with a rectangular hole in the front face of base unit 12 and is flush with the surrounding front face of base unit 12. Plate 68 carries a ball screw 74 mounted on bearings 76,76, and driven by a motor 78 which is also carried by plate 68. Coupled to ball screw 74 is a vial holder assembly 80 comprising a vial holder cup 82, a spool 84 driven by ball screw 74, and a connecting arm 86. Ball screw 74 and spool 84 together form an elevator which can raise or lower vial holder 82. Limit switches 88,90 are carried by plate 68 and contact spool 84 at the lowest position and highest or raised position, respectively, of vial holder assembly 80. In FIGS. 4a–4c, vial holder assembly 80 is shown in outline in the lowest position and is shown in solid lines (and in FIG. 4a in cross-section) in the highest position. Vial transporter 28 loads and unloads a vial into vial holder 82 at the lowest position. As the elevator raises the vial, a needle assembly 92 punctures the vial septum. Sampling of the vial contents occurs at the highest position, where the needle assembly 92 fully penetrates the vial. Needle assembly 92, well known in the art, has an inner needle with a port at its lower tip and an outer needle having a port higher up at point 94. At the highest position of the vial, the port at 94 remains above the level of the liquid specimen in the vial while the tip of the inner needle is submerged in the liquid specimen. The inner needle communicates with fitting 96, and the outer needle communicates with fitting 98. In operation, a volume of the liquid specimen is drawn through the center needle and conveyed via fitting 96 to a sparger unit 100 (see FIGS. 1 and 10) on base unit 12 or to an external sparger unit.

After a sampling operation, the sample flow path of device 10 permits flushing of the inner needle of assembly 92 with wash fluid such as water to reduce carryover by cleaning the inner surfaces of the inner needle. This is done with vial holder 82 vacant and in the highest position. A drain 102 is provided to drain the wash fluid expelled from the needle.

In order to reduce the vertical separation between the highest position and the lowest position of vial holder assembly 80 while still providing adequate clearance above vial holder 82 for loading and unloading vials, plate 68 has a slot 104 (FIG. 4a and 4d) through which arm 86 extends. The slot 104 has a narrow top portion and a lower portion with cam edges shaped and positioned relative to ball screw 74 to guide connecting arm 86 laterally as spool 84 moves vertically. As a vial and vial holder rise from the lowest position, the arm 86 rides against the cam edge 104a of slot 104. The arm enters the vertical section and the lateral motion of arm 86 and vial holder 82 is substantially complete when the needle assembly 92 penetrates the vial septum. When lowering the cam edge 104b of the slot 104 causes the lateral shift to the dotted position of vial holder 82 in FIG. 4c. Other known means such as a separate motor or piston can be used to perform the lateral shift. Cam slot 104 and connecting (follower) arm 86 form a simple and reliable mechanism without any additional motor.

Carried on ball screw 74 a small distance above spool 84 is a wiper arm 106, which moves in unison with spool 84 as the lead screw turns. As vial holder 82 is lowered after sampling, arm 106 pushes down on the vial end cap to strip the needles 92 if friction causes the vial to remain. When the vial holder assembly 80 reaches the lowest position, it can be seen in FIG. 4a arm 106 does not shift laterally because of its higher position on ball screw 74. The space above vial holder 82 is left free and accessible for loading or unloading a vial.

Figure 5C:
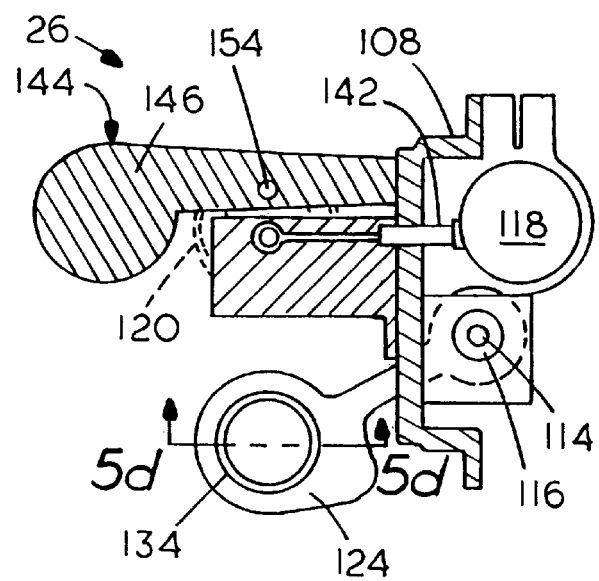
Figure 5D:
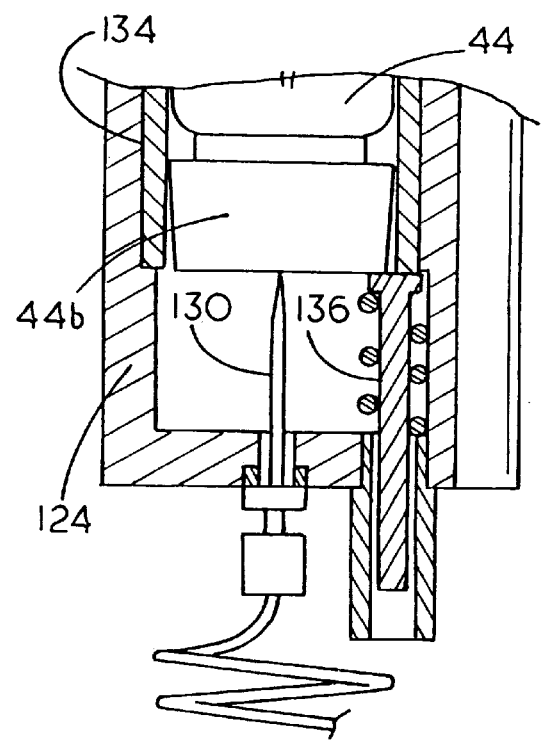

FIGS. 5a–5d show detail of sampling module 26. Module 26 has many elements that have the same function as corresponding elements of module 24. These elements include a plate 108, mounting holes 110, projecting face 112, ball screw 114, bearings 116, motor 118, vial holder assembly 120, spool 122, vial holder 124, connecting arm 126, limit switches 128 (the lower one being hidden behind holder 124 in FIG. 5a), and slot 131 in plate 108. Arm 126 extends through slot 131 and engages the edges 130a or 130b at the lower portion of slot 131 to laterally shift arm 126 and a vial carried in vial holder 124. In FIGS. 5a–5c, the lowest position of the vial holder (shown in solid lines and cross-section) is the vial load/unload position, and the highest position of the vial holder (shown in outline) is the sampling position.

As shown, a hollow lower needle 130 extends through the base of vial holder 120 for puncturing a lower vial septum in a vial 44 having end caps at both ends. Lower needle 130 fluidically communicates through flexible tubing to fitting 132. Vial holder 124 also has a heating sleeve 134 disposed therein to heat the specimen before or during sampling. Heating sleeve 134 has electrical power provided by wires carried on connecting arm 126 to central control circuit 66. Vial holder 124 also has a spring-loaded plunger 136 operable to keep the lower vial septum above the lower needle 130 when a vial is placed in the vial holder until the vial is raised and sampling occurs, and also to force the lower vial septum off the lower needle 130 after sampling.

Upper needle assembly 138 has an inner and outer needle similar to needle assembly 92, but the needles of assembly 138 are shorter so that their vent ports remain above the expected level of non-gaseous contents of the vial shown. The inner needle of assembly 138 communicates with line 140, and the outer needle communicates with line 142.

Sampling module 26 is further equipped with a magnetic sample stirring mechanism 144. Bracket 146 is affixed to plate 108 and holds a stir motor 148 that turns a primary magnet 150. A bar magnet 152, placed in the vial prior to loading the vial, is thereby induced to spin, mixing the contents of the vial. One type of double end vial useable with sampling module 26 is described in U.S. Pat. No. 5,147,551, herein incorporated by reference, although it is not the only type. Bracket 146 includes a spring-loaded plunger 154 (similar to plunger 136) for urging upper vial septum downward off needle assembly 138.

If either sampling module 24 or 26 is omitted from vial autosampler device 10, a plate can be provided to cover the port on the front panel of base unit 12 that is associated with the omitted module.

Figure 6A:
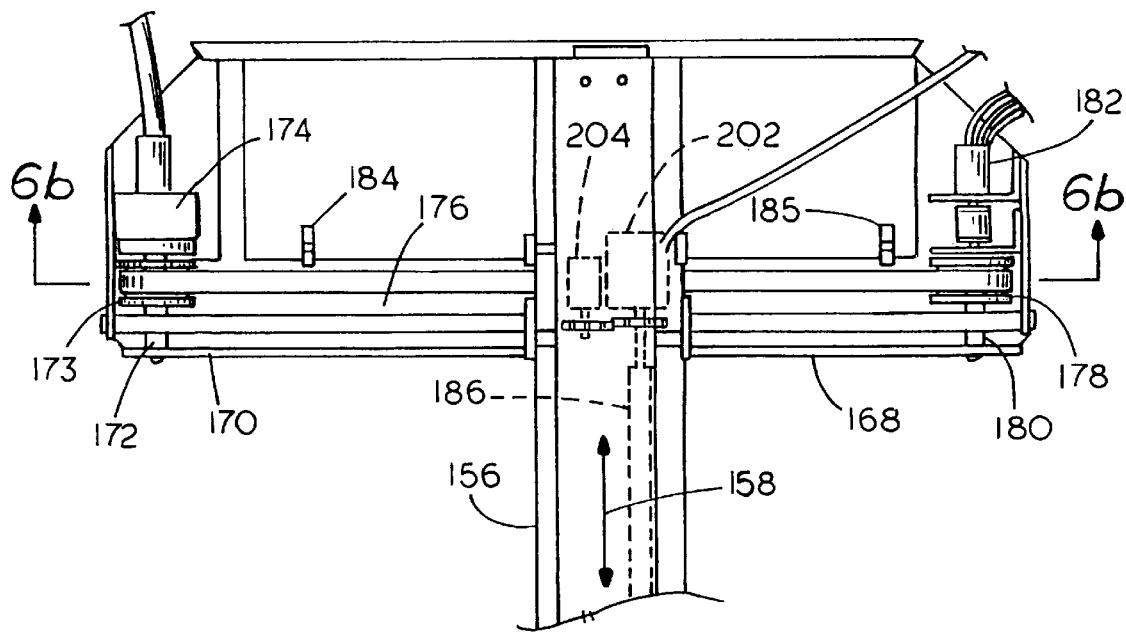
FIG. 6a shows a top partial view of a vial transporter according to the invention.
Figure 6B:
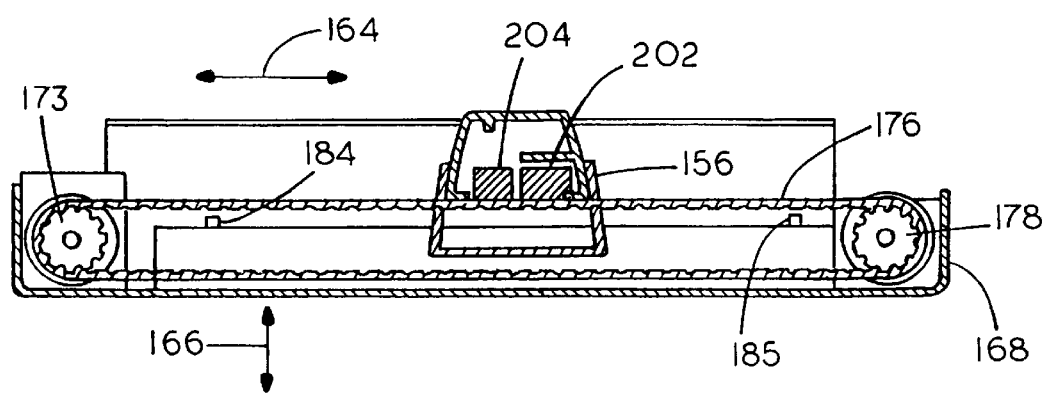
Figure 6C:
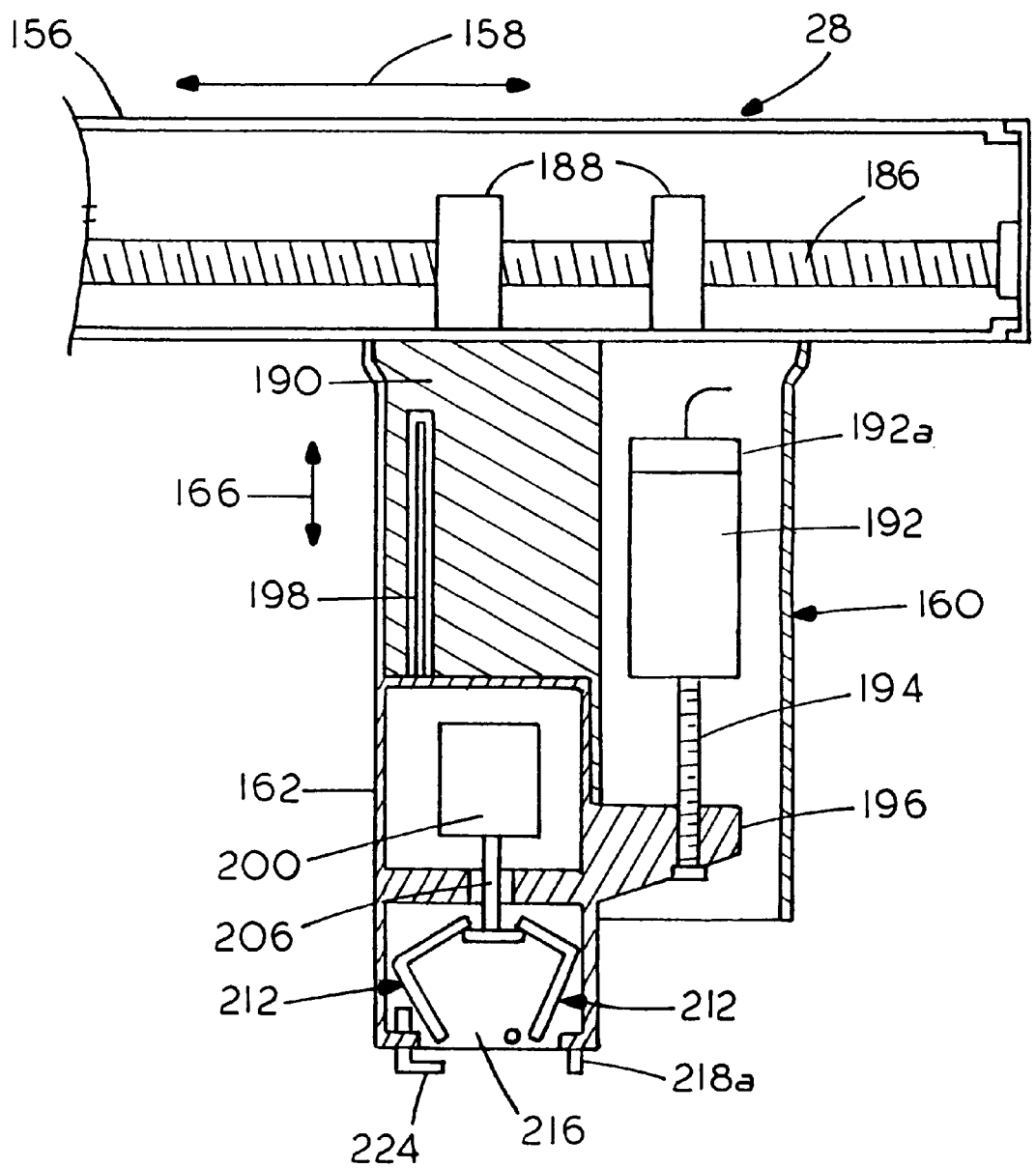
FIG. 6c shows a side sectional view of an end portion of a vial transporter according to the invention.

Another aspect of the invention is the vial transporter 28. Vial transporter 28, controlled by central control circuit 66, moves a vial between vial storage area 14, equilibration station 16, and sampling stations 20 and 22. Referring now to FIGS. 6a–6c, vial transporter 28 includes a main arm 156 extending along a first axis 158, a vial gripper assembly 160 adapted for movement along main arm 156, and a gripper head 162 which grasps vials by the upper end cap and which can be lowered and raised from gripper assembly 160. Main arm 156 is adapted for movement along a second axis 164, and the motion of gripper head 162 relative to gripper assembly 160 is along a third axis 166. The first, second, and third axes are substantially mutually perpendicular. Vial transporter 28 includes a tray 168 which is rigidly mounted inside base unit 12.

The tray 168 forms a module that can be inserted and removed from the base unit 12 so that the main arm 156 can be removed and replaced merely by unplugging the necessary electrical power and signal leads. The tray 168 has a front flange member 170 that is used for supporting a shaft 172 and pulley 173, driven from a controllable, variable speed reversible arm drive motor 174. The pulley 173 drives a belt 176 that is mounted over an idler pulley 178 mounted on an idler shaft 180 at an opposite end of the tray 168. The idler shaft 180 drives an encoder 182 that provides signals indicating the position of arm 156. Arm 156 clamps to belt 176 in a suitable manner, as shown in FIG. 6b, and moves laterally as indicated by the double arrow 164 as the belt 176 is driven. Limit switches 184 and 185 sense position of the arm 156 and provide signals to stop the motor 174 when the travel limit is reached.

A motor 202 drives screw 186, rotatably mounted in arm 156, as shown in FIG. 6c, and mounts a suitable drive block 188 that supports the gripper head 162. An encoder 204 senses the position of the vial gripper assembly 160 along screw 186 and provides a signal indicating the gripper position along the axis indicated by arrow 158.

A frame 190 is supported on the drive block 188. A drive motor 192 with an encoder 192a drives a vertical, rotatable screw 194 that threads through a lug 196 fixed to the frame to move gripper head 162, vertically as guided by a guide rod 198. Gripper head 162 mounts gripping fingers for gripping the tops of vials and transporting the vials when the main arm 156 is moved.

Figure 6D:
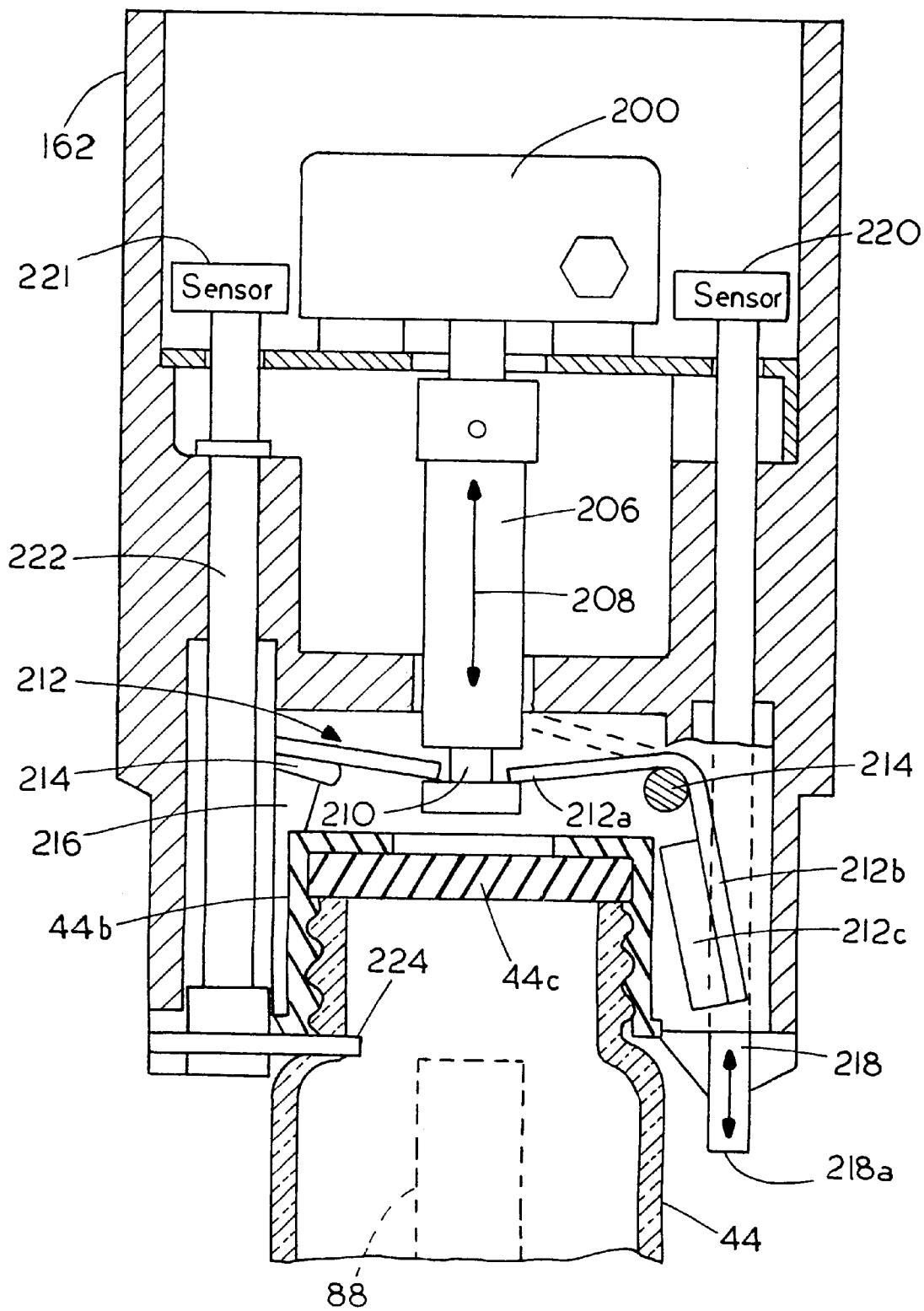
FIG. 6d is an enlarged sectional view of a vial gripper made according to the present invention.

Referring now to FIG. 6d, a solenoid actuator 200 linearly drives a drive tang 206 in a vertical direction 208. The outer end of drive tang 206 has an annular groove 210 formed therein. A plurality of gripper fingers 212 are mounted in a lower end 216 cavity of the gripper head, and are L-shaped, with an actuator end 212a that fits into the groove 210. There are at least three of the gripper fingers 212, around the periphery of the gripper head. The fingers are mounted on suitable pivot rods 214 that are fixed in the gripper head 162. The L-shaped gripper fingers 212 have outwardly extending finger ends 212b that include a grip pad 212c. Cavity 216 is of size to receive the upper portion and cap of a vial, as shown in FIG. 6d.

The actuator 200 is spring loaded to lift the ends 212a of the fingers 212 to the grip position shown in dotted lines. The finger ends 212b and the grip pads 212c then grip tightly onto the cap 44b on the neck 44a of a vial 44, so the vial is lifted by operating motor 192 through the screw 194.

The gripper head includes a sliding plunger 218 connected to a switch or sensor 220. When a plunger end 218a engages one of the dividers walls of a rack 30a, 30b as the gripper head 162 is lowered, the plunger 218 will move, and a signal will be delivered by the sensor 220 indicating the gripper is down. The actuator 200 is so the gripper fingers are open. A second plunger 222 is slidably mounted on the gripper head on the side opposite from the plunger 218, and a sensing foot 224 engages a shoulder of a vial when a vial is within the gripping fingers 212b. A sensor or switch 221 is actuated by plunger 222. The actuator 200 can then be de-energized so the fingers 212 pivot under spring load to grip a vial. It is apparent that the sensing foot 224 could engage the top of the vial cap if desired.

The signals from plunger 222 enables the motor 192 to lift a vial and transport it to the appropriate station. The gripper head 162 operates to deliver vials to and from the equilibration, identification and respective sampling stations under control of control circuit 66. The plunger 222 also provides a signal that a vial has been released so that the gripper head can be further operated after a vial is deposited in a vial holder at a sampling station, for example. The gripper is a fail safe unit and actuator 200 will remain in its gripping position if there is a loss of power.

The position of each of the vials in the vial rack is preprogrammed into the control unit 66, in the basis of x and y coordinates. The encoders 182 and 204 give the x, y position of the gripper head. An encoder on motor 192 gives the z position.

Figure 11:
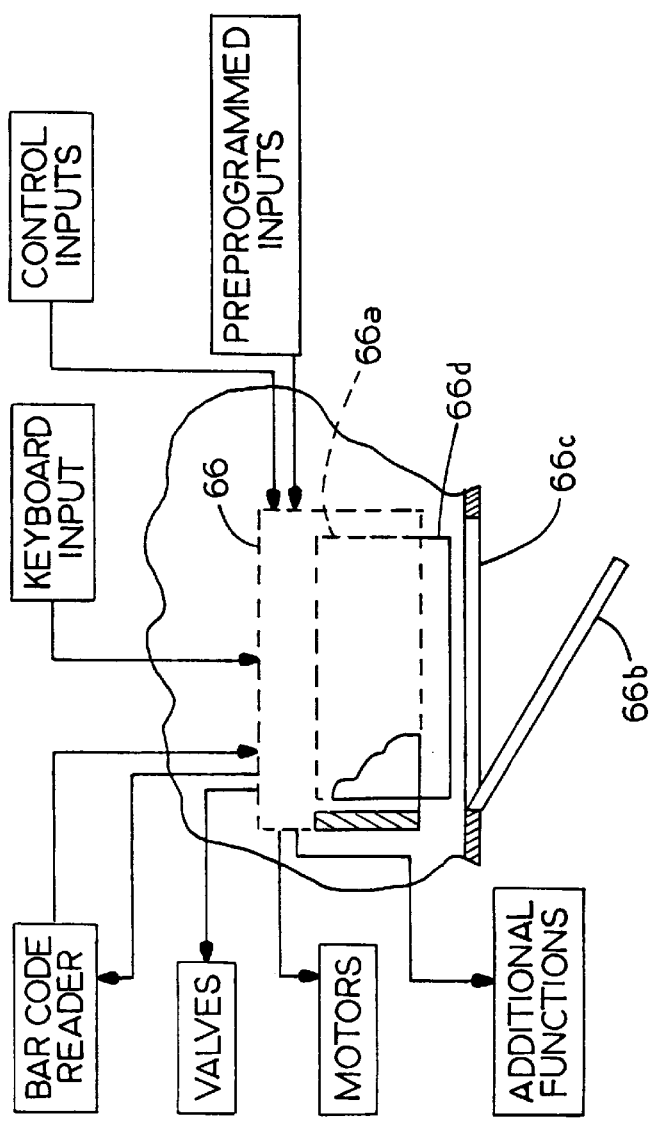
FIG. 11 is a sectional view of an access panel for a control circuit in accordance with the invention.

Referring to FIG. 11, a schematic representation of an access in the front panel of the base unit is shown, for access to the central control circuit 66 has a plug in slot or port 66a for a removable circuit module such as a memory card 66d. An access door 66b shown in both FIGS. 1 and 11 is provided, to open an opening 66c in the front panel of the base unit 12. The opening 66c aligns with the slot for the plug in circuit module 66d that is shown partially removed in FIG. 11, so that for different sampling programs, the memory card or module 66 can be removed and replaced with another module. The access door 66b can have a simple push latch, that will release when pushed, and then latch again when the door is closed. This will permit easy maintenance of various programs for running different samples, utilizing different combinations of the sampling modules that are available without reprogramming.

Figure 12:
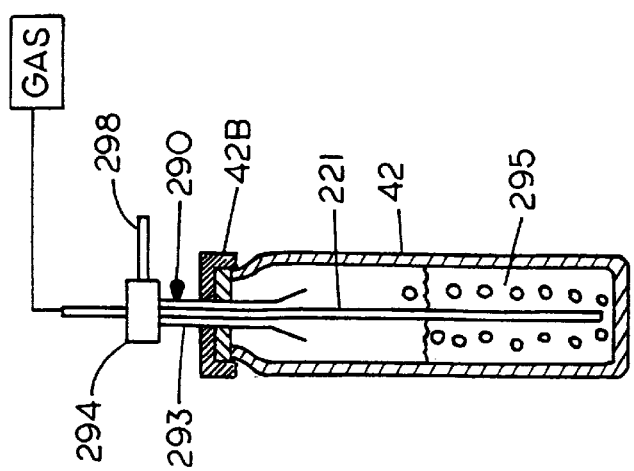
FIG. 12 is a schematic sectional view of a single ended vial utilizing an alternate form of mixing soil samples for use with the present invention.

FIG. 12 illustrates the use of the single ended vial in the soil sample module, where the sample is sparged utilizing a double needle as illustrated. The vial 42 has a septum that is shown only schematically, and the needle assembly indicated at 290 includes a central hollow needle 292 and an outer tubular concentric needle 293 that are separated fluidly, with a cap 294 on the outer needle 293 to receive gaseous material being expelled from the vial. A sample of a soil suspension 295 is at a level approximately half way up the vial as shown, and the long needle 292 has an outlet end close to the bottom of the vial so that when gas is introduced from the source it will bubble through the sample and will agitate and mix the sample well by the bubbling effect.

Figure 8:
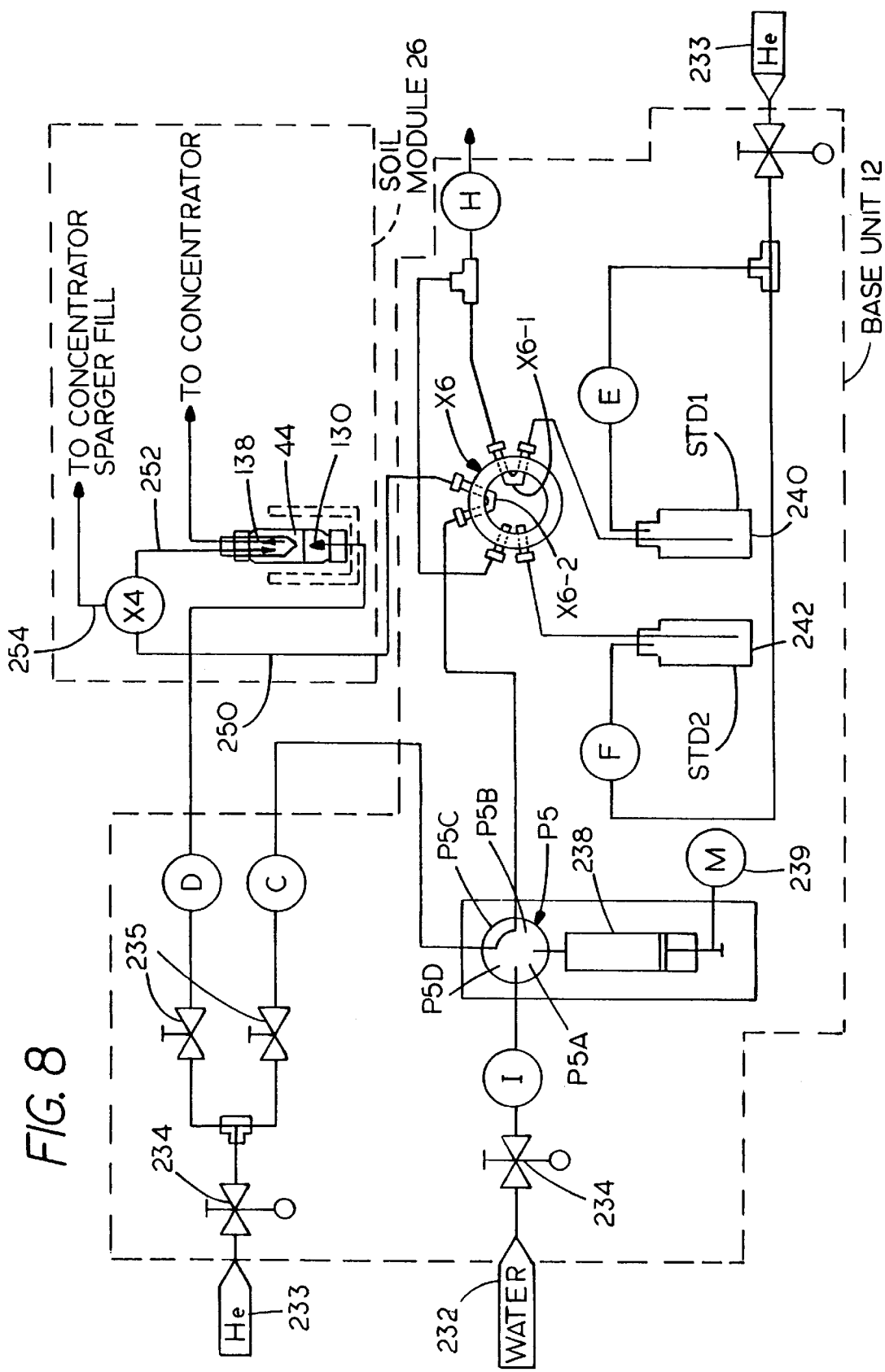
FIG. 8 is a diagrammatic view of a flow path of the device of FIG. 1 where only another sampling module is installed.

The volatiles in the soil will escape into the headspace above the liquid level, and will pass out through the outer needle 293 into the cap 294 and then be delivered to a sample line 298 for delivery to the purge and trap unit, or to the plumbing and glassware that is shown in FIG. 8 for example. This eliminates the need for the double needle and a frit in the vial, and does not require a magnetic stirring device. The agitation or stirring of the bubbling gas coming from the long needle 221 that is submerged into the sample adequately agitates the sample to obtain good results from the volatiles in the soil.

The operations of removing samples from the vials that are placed in the respective sampling stations 20 and 22 are sequential steps. A number of valves are operated in a procedure for each type of sample. The valves can be mounted on the base unit in any desired location and are well known solenoid valves, but are adapted to provide particular flow paths and individual operations for carrying out the desired functions. The valves are shown schematically in FIGS. 7, 7a, 8, 9, and 9a.

Figure 7:
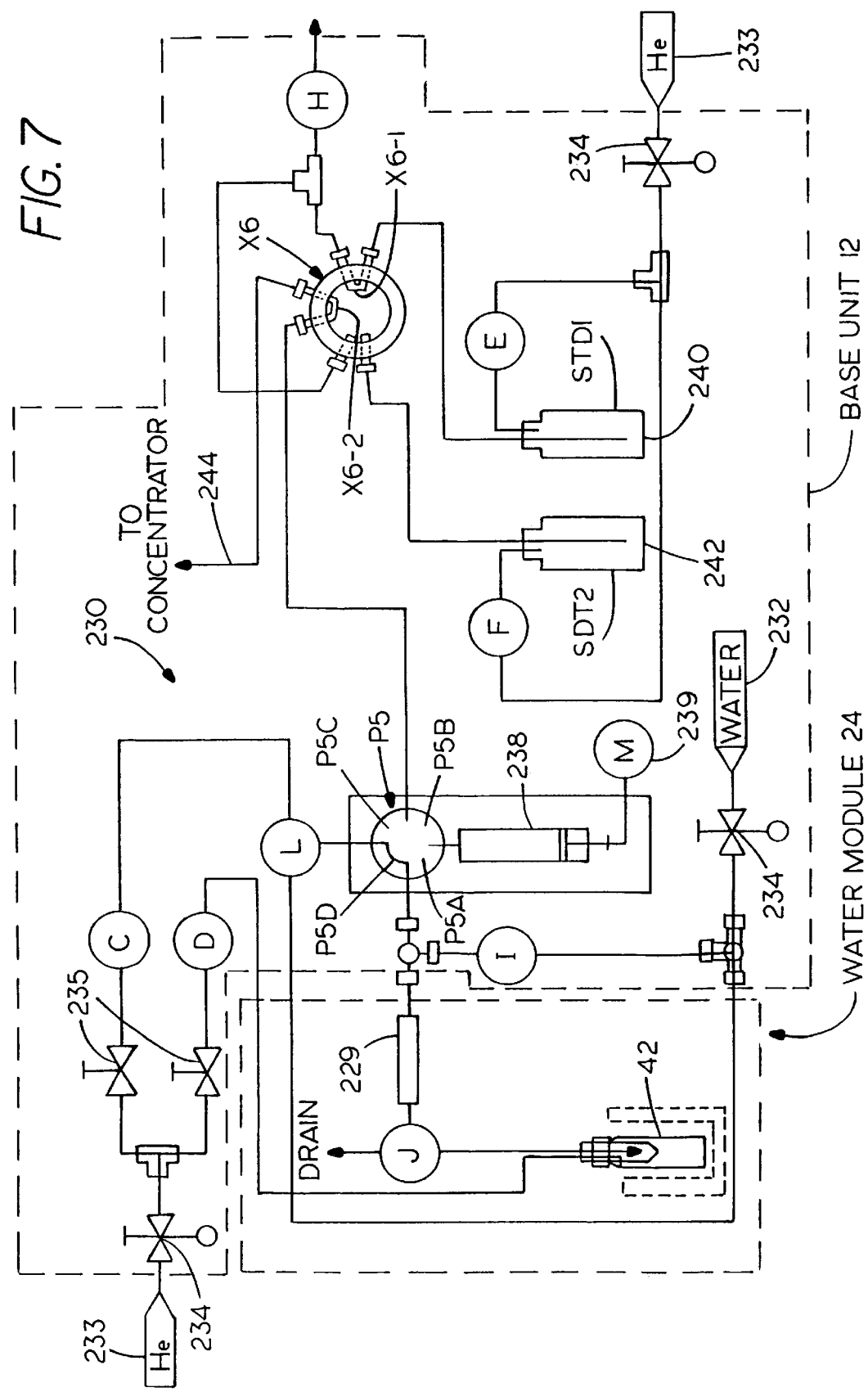
FIG. 7 is a diagrammatic view of a flow path of the device of FIG. 1 where only one sampling module is installed.
Figure 7A:
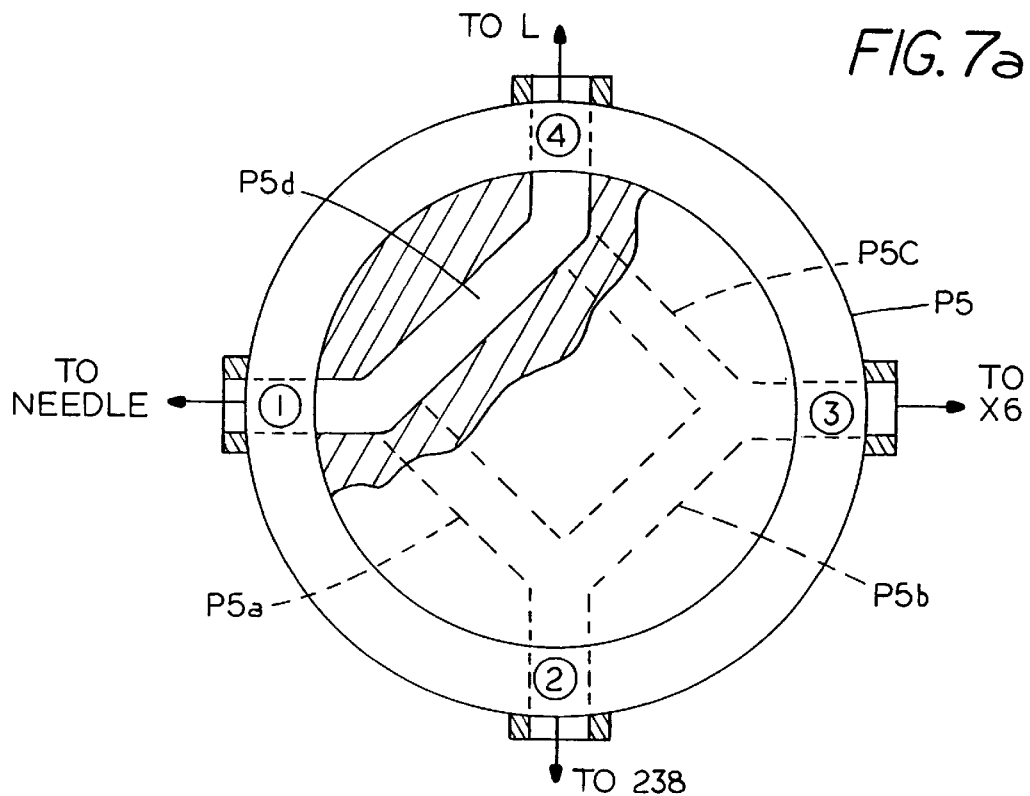
FIG. 7a is an enlarged schematic representation of a selector valve used in FIG. 7.

FIG. 7 schematically illustrates the arrangement used for sampling liquid or water samples in the station 20. Once a vial has been properly identified using the bar code reader, and equilibrated, and is placed by the vial transporter 28, the into the cup type vial holder 82 of sampling module 24, sampling a liquid or water sample is conducted using the fluid circuit of FIG. 7. A sequence of operations for various functions is set forth in Table I, for simplicity of understanding of actuation or states of the various valves and other components.

In all of the sequences that are illustrated, it is important to note that the system permits backflushing the needles with a water or liquid to remove previous sample traces, utilizing the cup type vial holders to collect the backwash liquid and drain it as previously discussed and shown. A multi port chromatograph valve is utilized to permit selectively adding a known volume of two different standards into the test sample.

The samples are transferred to a purge and trap concentrator to purge the volatiles into a sorbent trap, which is then heated and swept with a carrier gas into a gas chromatograph column for separation and detection. Thus the outlet conduits labeled "to concentrator" means that these are connected to existing instruments that are well known for processing and subsequent analysis. A Model 3000 purge and trap concentrator made by Tekmar Company of Cincinnati, Ohio is useful or the sparging unit 100 can be used.

Referring first to FIG. 7, several common elements in the glassware, valving and conduit will be explained in connection with FIG. 7 and will be numbered identically in subsequent figures for different processes. The water module connections and piping are shown generally at 230 and are outlined in dotted lines as are components on the base unit 12. A source of water 232, helium 233 and lines with pressure regulators 234 and flow controllers 235 are provided.

On-off valves C and D control a source of helium 233. Valve D connects to the outer needle assembly 92 in a water sample vial 42 held in vial holder 82. Valve C connects through a valve L to a solenoid operated multiple port valve P5 operated to four different connections in response to control signals to connect any two adjacent valve ports. For explanation purposes, the valve P5, also shown in FIGS. 1 and 7a, has a first position P5A that connects the ports 1 and 2; a second position P5B that connects ports 2 and 3; a third position P5C that connects ports 3 and 4, and as shown in FIG. 7 a fourth position P5D connecting ports 4 and 1. This valve is a conventional valve that has a center block that will connect the adjacent ports as desired by moving to the positions P5A, P5B, P5C, and P5D.

Port 2 of valve P5 is connected to a commercially available syringe or pump 238 (See also FIG. 1) which has an inner plunger that is driven by an external motor 239 of any desired form. The syringe pump 238 receives and discharges samples under control of motor 239 when valve P5 is at its desired location.

Valve L connects to port 4 of valve P5, and port 1 is connected through a filter 239 to a valve J connected to the inner (sampling) needle of needle assembly 92 in vial 42. Valve I leads from the water source 232 to a "t" connection between filter 229 and valve P5. Valve L also has a port connected to the water source 232.

The port 2 of P5 connects to the outlet of the syringe pump 238. Port 3 of P5 connects to a port of a multi-port chromographic valve X6, used for adding a known volume of a standard into a sample that is delivered to a concentrator such as the purge and trap concentrator.

A first standard source vial 240, and a second standard source vial 242 are fluidly coupled by conduits through valves E and F, respectively, to separate ports on valve X6. These vials can be used for providing matrix.

Figure 7B:
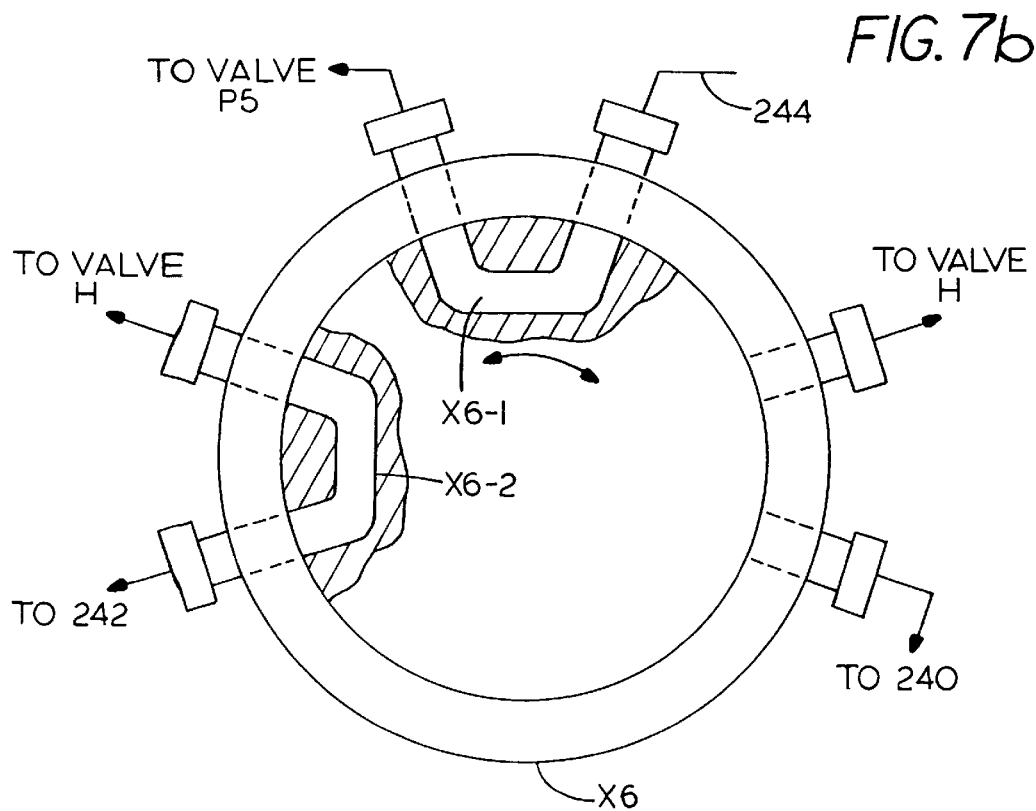
FIG. 7b is a schematic enlarged sectional view of a multi port chromatographic valve used in the flowpath of the present invention.

The multi port chromographic valve X6 is a stepper type rotary solenoid valve that has an internal block that can be rotated 90°, and which has two schematically shown U-shaped internal channels X6-1 and X6-2 (see also FIG. 7b). Channel X6-1 connects the internal standard source 240 port to the port leading to valve H which leads to drain.

In FIG. 7 U-shaped channel X6-2 connects port 3 of valve P5 through a port of X6 to line 244. Valve X6 rotates 90° counter clockwise under control of circuit 66 and then as shown in FIG. 7b, channel X6-2 connects the second or surrogate standard source 242 to valve H. The U-shaped channel X6-1 then connects port 3 on valve P5 to line 244. Those are the two operable positions of valve X6.

The sequence of operation is shown in Table I below. In Table I, and the subsequent operation tables, the individual valves designated by capital letters are considered to have two positions. "0" designates off, and "1" equals on, in the table columns. The P5 valve connections or positions P5A–P5D, are designated by the letter (A–D) in the table column.

Valve X6 is indicated by position A shown in solid lines in FIG. 7, and in position B it is rotated 90° and shown in FIG. 7b. Additionally, in certain instances, the "vial mechanical position" column shows whether the vial holder and vial is up (U) (pierced by the sample needle) or down (D).

TABLE I

Water System - Water Module Only

| Mode of Operation | C | D | E | F | H | I | J | L | Vial Mech pos. | X6 | P5 |
|---|---|---|---|---|---|---|---|---|---|---|---|
| STANDBY AND WAIT FOR PURGE READY | 0 | 0 | 0 | 0 | 0 | 0 | 0 | 0 | D | A | D |
| PREPURGE | 1 | 1 | 0 | 0 | 0 | 0 | 0 | 0 | D | A | D |
| RAISE VIAL | 0 | 0 | 0 | 0 | 0 | 0 | 0 | 0 | U | A | D |
| FILL SYRING | 0 | 1 | 0 | 0 | 0 | 0 | 0 | 0 | U | A | A |
| FILL STD. 1 | 0 | 0 | 1 | 0 | 1 | 0 | 0 | 0 | U | A | A |
| TRANS SAMPLE STD 1 | 0 | 0 | 0 | 0 | 0 | 0 | 0 | 0 | U | B | B |
| SWEEP TRANS LINE | 1 | 0 | 0 | 0 | 0 | 0 | 0 | 0 | U | A | C |
| FILL STD 2 | 0 | 0 | 0 | 1 | 1 | 0 | 0 | 0 | U | B | D |
| TRANS SAMPLE STD 2 | 0 | 0 | 0 | 0 | 0 | 0 | 0 | 0 | U | A | B |
| SWEEP TRANS LINE | 1 | 0 | 0 | 0 | 0 | 0 | 0 | D | A | C | |
| RINSE SYRINGE | 0 | 0 | 0 | 0 | 0 | 1 | 1 | 0 | U | A | A |
| DRAIN SYRINGE | 0 | 0 | 0 | 0 | 0 | 0 | 1 | 0 | U | A | A |
| BACKFLUSH FILTER | 0 | 0 | 0 | 0 | 0 | 1 | 1 | 0 | U | A | C |
| RETURN VIAL TO TRAY | 0 | 0 | 0 | 0 | 0 | 0 | 0 | 0 | D | A | C |
| FLUSHING NEEDLE | 0 | 0 | 0 | 0 | 0 | 1 | 0 | 0 | U | A | C |
| WAIT FOR DESORB | 0 | 0 | 0 | 0 | 0 | 0 | 0 | 0 | D | A | D |
| RINSE GLASSWARE | 0 | 0 | 0 | 0 | 0 | 0 | 0 | 1 | D | A | D |
| PURGE GLASSWARE | 1 | 0 | 0 | 0 | 0 | 0 | 0 | 0 | D | A | C |

At the cycle start (standby) and waiting for a purge ready signal from the concentrator or other instrument that it is ready to receive a sample the components are in the same condition. The vial is down, and valve P5 is in the solid line position P5D. In the prepurging stage, valves C and D open, and helium is provided through valves D, L, P5, and J to flow out the needles. The vial is raised to engage the needle, with the valves all closed. Filling the syringe as the syringe plunger retracts has valve D open and valve P5 shifted to position P5A connecting port 1 to port 2 to the syringe or pump 238.

Standard filling is by opening valve H and valve E. Channel loop X6-1 fills with standard 1. Standard in loop X6-1 and one half of the sample are transferred by moving valve X6 90° to position "B" to connect channel X6-1 between valve P5 in position P5B and line 244. The syringe or pump 238 discharges ½ the sample through the valve X6 and line 244, carrying with it the quantity of standard 1 in channel X6-1 to line 244 and the concentrator.

Standard 2 is filled by moving valve P5 to position P5D, opening valves F and H (to drain) so a quantity of standard 2 fills loop X6-2. Transferring standard 2 occurs with valve P5 moved to position P5B, valve X-6 moved to position A, and the remaining portion of the sample contained in the syringe or pump 238 discharged by motor 239 through loop X6-2 into line 244.

The two halves of the sample, and the different standards, (which can be selectively added) have thus been sent to the concentrator, for handling and for subsequent analysis. The transfer line is swept as valve C opens and valve P5 moves to the P5C position, connecting valve L to valve X6 and thus to line 244 for flushing through valve X-6.

The syringe is rinsed with water; valve I is open, valve J is open (to drain) and valve P5 is moved to the P5A position. The syringe is retracted to fill with water.

The syringe or pumper 238 is then drained by shutting off valve I but leaving valve J connected to drain and moving the syringe plunger up. The filter is backflushed by opening valves I and J and moving valve P5 in its P5C position.

The vial is lowered by operating the vial elevator and the vial transporter removes the vial from holder 82 and returns it to the tray. The vial holder 82 is preferably raised again and the inner needle is flushed with water by opening the valve I and leaving valve P5 in the P5C position. Water will flush through the inner needle to insure no carryover and will be contained and drained from the vial holder.

The needle may be purged if desired, through P5 by opening valve C with valve J off. While waiting for a desorb signal from the concentrator or test apparatus, the unit is essentially at rest with the valve P5 in its position P5D. The glassware conduits are liquid rinsed by opening the valve L to the water source, and connecting through valve P5 and valve X6 to line 244. The vial holder is down for reloading a vial. Helium is purged through the glassware by opening valve C after closing valve L and moving P5 to position P5C.

The cycle will then repeat, as desired for each additional vial that is lifted in the appropriate station for the water module.

It should be noted that if only one of the standards is injected into the sample per run, movement of valve X6 will place one of the channels X6-1 or X6-2 open to the other standard source, and such channel may then be flushed clean during the desorb cycle. The appropriate channel X6-1 or X6-2 is between valve P5 and line 244 during the syringe rinse and purge cycles.

Utilizing the second module 26, which comprises a soil module is as shown in FIG. 8. The soil module as shown is using a double ended vial 44, with a lower needle 130 and an upper double needle assembly. A single ended vial can be used.

The mode of operation of the various components is shown in Table II. The addition of the valve X4, which directs the sample in various conditions also is seen. The conduit connections are somewhat different as will be described. The helium source 233 is shown, along with the valves C, D, E, F, P5, X6, standard 1 source 240 and standard 2 source 242. The valve D is connected directly to the lower needle 130 shown in FIG. 8. The vial 44 is held in the vial holder. The valve X4, in its "on" position indicated by a 1 in Table II, connects line 250 from valve X6 to the inner needle of the needle assembly 138 through line 252. When valve X4 is "off" it connects the conduit of the line 250 to the output line 254 leading to the concentrator.

TABLE II

Soil System - Soil Module Only

| Mode of Operation | C | D | E | F | H | I | ViaL Mech pos. | P5 | X4 | X6 | Stir |
|---|---|---|---|---|---|---|---|---|---|---|---|
| STANDBY AND WAIT FOR PURGE READY | 0 | 0 | 0 | 0 | 0 | 0 | D | D | 0 | A | 0 |
| PREPURGE | 1 | 1 | 0 | 0 | 0 | 0 | D | C | 1 | A | 0 |
| RAISE VIAL | 0 | 0 | 0 | 0 | 0 | 0 | U | C | 0 | A | 0 |
| FILL SYRINGE | 0 | 0 | 0 | 0 | 0 | 1 | U | A | 0 | A | 0 |
| FILL STD 1 | 0 | 0 | 1 | 0 | 1 | 0 | U | B | 0 | A | 0 |
| TRANS WATER STD 1 | 0 | 0 | 0 | 0 | 0 | 0 | U | B | 1 | B | 0 |
| SWEEP TRANS LINE | 1 | 0 | 0 | 0 | 0 | 0 | U | C | 1 | A | 0 |
| FILL STD2 | 0 | 0 | 0 | 1 | 1 | 0 | U | B | 1 | B | 0 |
| TRANS WATER STD 2 | 0 | 0 | 0 | 0 | 0 | 0 | U | B | 1 | A | 0 |
| SWEEP TRANS LINE | 1 | 0 | 0 | 0 | 0 | 0 | U | C | 1 | A | 0 |
| PREHEAT/ STIR | 0 | 0 | 0 | 0 | 0 | 0 | U | C | 0 | A | 0 OR 1 |
| PURGE VIAL | 0 | 1 | 0 | 0 | 0 | 0 | U | C | 0 | A | 1 |
| WAITING FOR DESORB | 0 | 0 | 0 | 0 | 0 | 0 | U | C | 0 | A | 0 |
| FILL SYRINGE | 0 | 0 | 0 | 0 | 0 | 1 | U | A | 0 | A | 0 |
| RINSE LINES | 0 | 0 | 0 | 0 | 0 | 0 | U | B | 0 | A | 0 |
| PURGE LINE | 1 | 0 | 0 | 0 | 0 | 0 | U | C | 0 | A | 0 |
| RETURN VIAL TO TRAY | 0 | 0 | 0 | 0 | 0 | 0 | D | C | 0 | A | 0 |

At standby and purge ready, the vial is in its down position, valve P5 is in the P5D position, valve X4 connects lines 250 and 254, and valve X6 is in the A position.

It should be noted that in Table II there is an additional column relating to the "stir" cycle for magnetic stirring of bar 152. In the prepurge cycle, helium source 233 is open through valve P5 and valve X6, through line 250 and X4 in its "on" position into the needle assembly 138 and from valve D through needle 130 as shown in FIG.8.

The vial is raised after valve C and D close so needles 138 and 130 pierce the respective septums in vial 44, which contains soil for sampling. Syringe 238 is retracted and filled from source 232 through valve I and valve P5 in its P5A position.

Filling standard 1 is the same as described in Table I. The transfer of water and standard 1 is with valve X4 in its "on" position connecting lines 250 and 252 and expelling one half of the syringe volume into vial 44. Standard 2 is loaded with the appropriate movement of the valve X6 and transferred with the remaining water from syringe 238. The transfer line is swept and the stir bar is activated to stir the soil sample, the water, and the standards. Heating can take place at this time. The stir bar can continue to operate as long as desired.

The vial is then purged or sparged by opening valve D. Helium from needle 130 bubbles through the frit in the vial 44, while valve P5 blocks return through valve X6. The volatiles are carried to the concentrator with the purge gas through one needle of assembly 138 and the appropriate line. The syringe 238 is filled, when valve I opens, and the plunger retracts with valve P5 in its P5A position and the valve X4 off.

At the rinsing line (conduit) step liquid in the syringe 238 is expelled utilizing the motor 239, with the valve P5 in the P5B position, flushing the line 250, and with valve X4 in its "off" position, also flushing the line 254 to remove carry-over. Line purge has valve C open, and valve P5 in its P5C position and valve X4 connects to lines 250 and 254. The vial is lowered and returned to its tray. The unit is ready for a new cycle.

Figure 9:
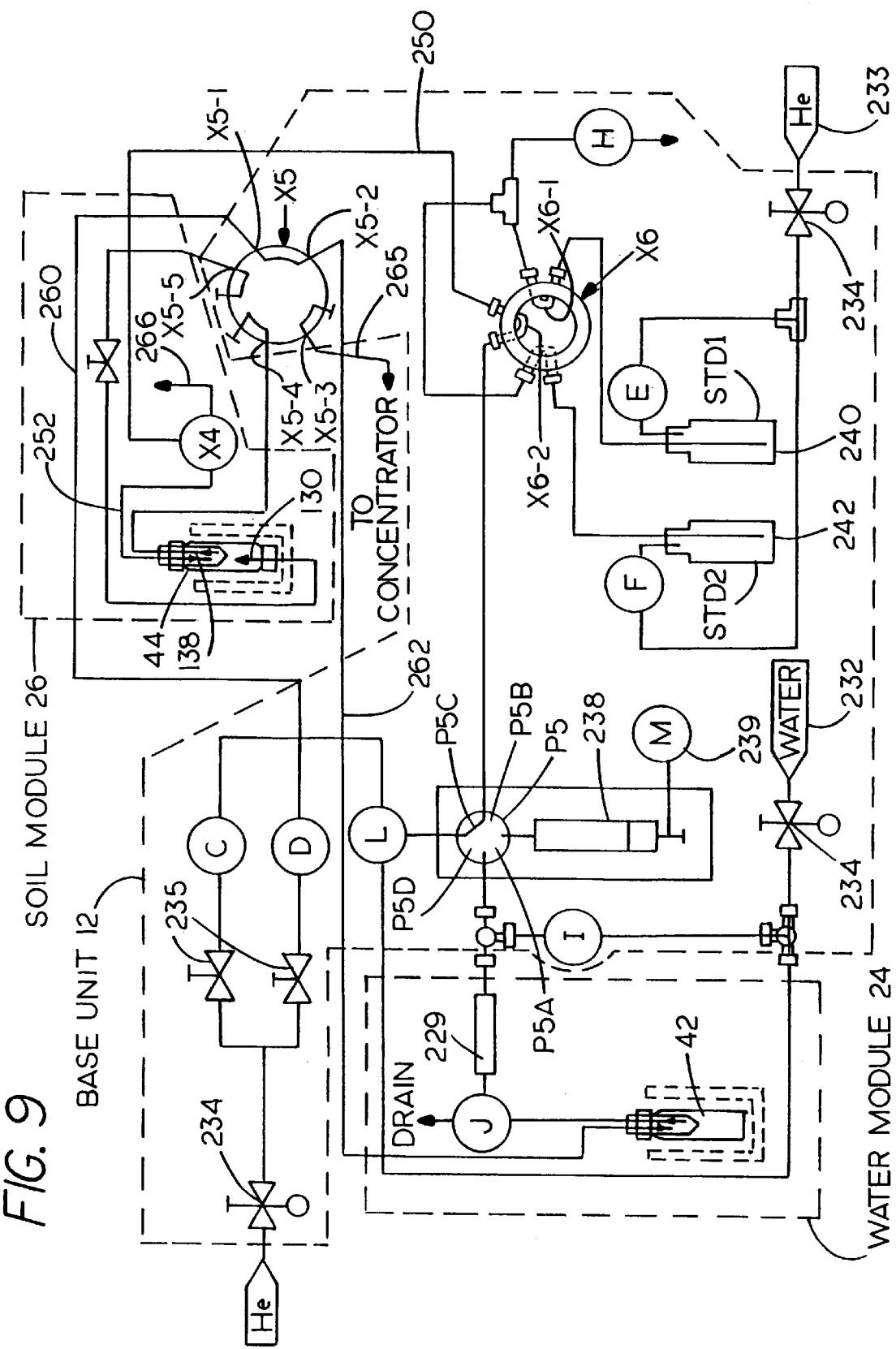
FIG. 9 is a diagrammatic view of a flow path of the device of FIG. 1 where both sampling modules are installed.
Figure 9A:
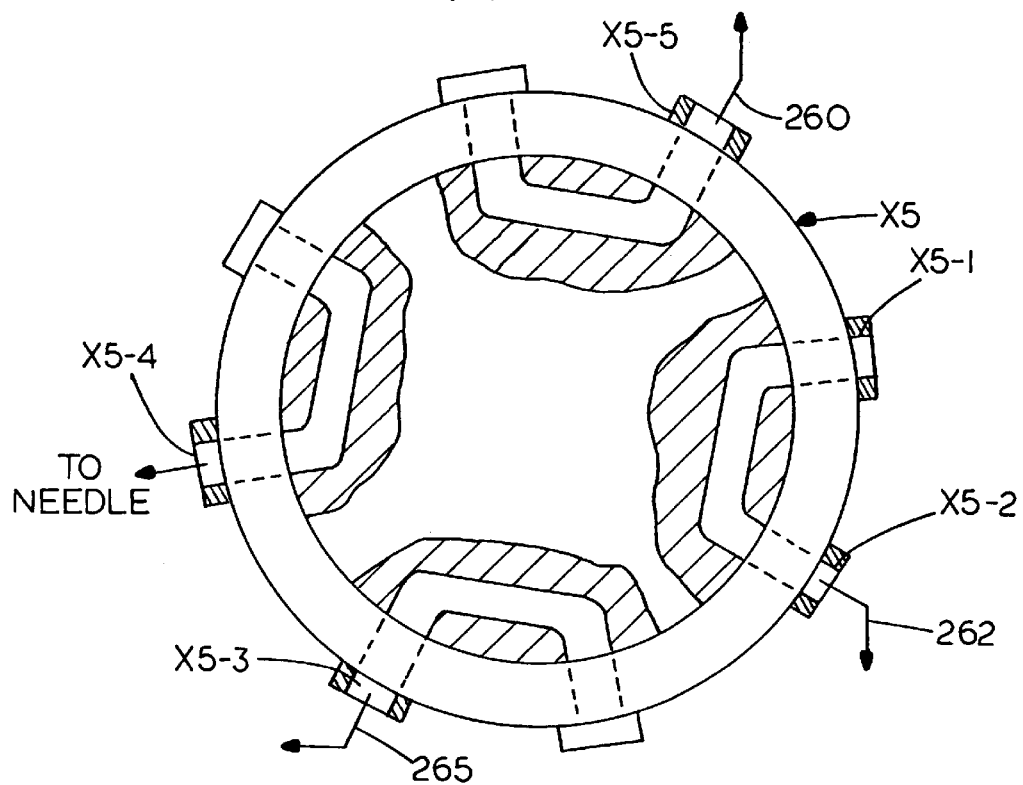
FIG. 9a is an enlarged schematic view of a selector valve used in one embodiment of the present invention.

FIG. 9 illustrates a system with an interconnect valve used so both the soil and water modules can be mounted on the base unit, (indicated in dotted lines) and the plumbing will interconnect the two so that either soil or water sampling can occur. The samples cannot be run simultaneously. In FIG. 9, the valves shown in FIG. 7 and the valves shown in FIG. 8 are all included, and in addition a valve X5 is used. This is a multi-position connecting valve that will be used for permitting either soil or water samples to be obtained from the respective modules.

The valve X5 is a rotary solenoid control valve that can provide for multiple port connections. As shown, the valve has ports X5-1, X5-2, X5-3, X5-4 and X5-5 that are operable. Other ports can be used for dead ending connections as is shown illustratively. As shown in solid lines in FIG. 9 valve X5 has port X5-4 and X5-5 dead ended, as well as X5-3.

The unit in FIG. 9 is connected in solid lines as it would be for running water samples, and the valve X5 will stay in the same position during all of the running of water samples, and it can be seen that the vial 44 and its connecting needles, are out of the circuit completely. Valve X4 stays off and connects line 250 to output line 266.

The description of the operation of the water/soil combination system when running from the water module is illustrated in Table III, and it does essentially all of the steps that were previously described in connection with Table 1, and the placement of the valves are essentially the same, except that valve D is connected through valve X5 to the needle in vial 42, rather than directly. The conduit shown at 260 leads to port X5-1 of valve X5, and connects at port X5-2 to a line 262 connected to the needle assembly for the water sample vial.

In this instance, the same liquid needle flush is available. The valve conditions are shown in Table III.

TABLE III

| | W/S System-Running Water | | | | | | | | | | | | | |
|---|---|---|---|---|---|---|---|---|---|---|---|---|---|---|
| Mode of Operation | C | D | E | F | H | I | J | L | X3 | X5 | X6 | Vial pos. | P5 | Stir |
| STANDBY AND WAIT FOR PURGE READY | 0 | 0 | 0 | 0 | 0 | 0 | 0 | 0 | 0 | 1–2 | A | D | C | 0 |
| PREPURGE | 1 | 1 | 0 | 0 | 0 | 0 | 0 | 0 | 0 | 1–2 | A | D | C | 0 |
| RAISE VIAL | 0 | 0 | 0 | 0 | 0 | 0 | 0 | 0 | 0 | 1–2 | A | U | C | 0 |
| FILL SYRINGE | 0 | 1 | 0 | 0 | 0 | 0 | 0 | 0 | 0 | 1–2 | A | U | A | 0 |
| FILL INTERNAL STD 1 | 0 | 0 | 1 | 0 | 1 | 0 | 0 | 0 | 0 | 1–2 | A | U | B | 0 |
| TRANS SAMPLE STD 1 | 0 | 0 | 0 | 0 | 0 | 0 | 0 | 0 | 0 | 1–2 | B | U | B | 0 |
| SWEEP TRANS LINE | 1 | 0 | 0 | 0 | 0 | 0 | 0 | 0 | 0 | 1–2 | A | U | C | 0 |
| FILL STD 2 | 0 | 0 | 0 | 1 | 1 | 0 | 0 | 0 | 0 | 1–2 | B | U | B | 0 |
| TRANS SAMPLE/ STD 2 | 0 | 0 | 0 | 0 | 0 | 0 | 0 | 0 | 0 | 1–2 | A | U | B | 0 |
| SWEEP TRANS LINE | 1 | 0 | 0 | 0 | 0 | 0 | 0 | 0 | 0 | 1–2 | A | U | C | 0 |
| RINSE SYRINGE | 0 | 0 | 0 | 0 | 0 | 1 | 1 | 0 | 0 | 1–2 | A | U | A | 0 |
| DRAIN SYRINGE | 0 | 0 | 0 | 0 | 0 | 0 | 1 | 0 | 0 | 1–2 | A | U | A | 0 |
| BACKFLUSH FILTER | 0 | 0 | 0 | 0 | 0 | 1 | 1 | 0 | 0 | 1–2 | A | U | C | 0 |
| RETURN VIAL TO TRAY | 0 | 0 | 0 | 0 | 0 | 0 | 0 | 0 | 0 | 1–2 | A | D | C | 0 |
| FLUSH NEEDLE | 0 | 0 | 0 | 0 | 0 | 1 | 0 | 0 | 0 | 1–2 | A | U | C | 0 |
| WAIT FOR DESORB | 0 | 0 | 0 | 0 | 0 | 0 | 0 | 0 | 0 | 1–2 | A | D | D | 0 |

TABLE III-continued

W/S System-Running Water

| Mode of Operation | C | D | E | F | H | I | J | L | X3 | X5 | X6 | Vial pos. | P5 | Stir |
|---|---|---|---|---|---|---|---|---|---|---|---|---|---|---|
| RINSE GLASSWARE | 0 | 0 | 0 | 0 | 0 | 0 | 0 | 1 | 0 | 1–2 | A | D | C | 0 |
| PURGE GLASSWARE | 1 | 0 | 0 | 0 | 0 | 0 | 0 | 0 | 0 | 1–2 | A | D | C | 0 |

The combination arrangement for plumbing the water and soil samples when soil samples are to be run is shown in Table IV. The valve X5 moves to different positions during operation for testing soil when both the water module and soil module are incorporated. First, valve X5 will be connecting ports X5-1 and X5-5. In the prepurge step helium then will be passed through valve L, the valve P5 at the P5C position through valve X6, and through line 250 to valve X4 with the valve X4 in its on position connected to line 252 leading to the needle assembly, helium will flow through the system. Additionally, valve D will be connected through ports X5-1 and X5-5 to the lower needle 130.

Standard 1 fill, transferring water/standard 1, standard 2 fill, and transferring water/standard 2 operate as previously explained, and half of the syringe volume is used for transferring the respective standards into the vial 44 with the valve X4 in its position connecting line 250 to 252 and thus to the needle assembly.

In the sweeping transfer line step shown in Table IV, helium is introduced from valve C through the lines leading to valve P5 in its P5C position, valve X6, line 250, valve X4 and then into the vial 44.

Preheating, stir purging vial, and other steps are the same as previously explained, with the valve X5 position being

TABLE IV

W/S System-Running Soil

| Mode of Operation | C | D | E | F | H | I | J | L | X3 | X5 | X6 | Vial pos. | P5 | Stir |
|---|---|---|---|---|---|---|---|---|---|---|---|---|---|---|
| STANDBY AND WAIT FOR PURGE READY | 0 | 0 | 0 | 0 | 0 | 0 | 0 | 0 | 0 | 1–5 | A | D | C | 0 |
| PREPURGE | 1 | 1 | 0 | 0 | 0 | 0 | 0 | 0 | 1 | 1–2 | A | D | C | 0 |
| RAISE VIAL | 0 | 0 | 0 | 0 | 0 | 0 | 0 | 0 | 0 | 1–2 | A | U | C | 0 |
| FILL SYRINGE | 0 | 0 | 0 | 0 | 0 | 1 | 1 | 0 | 0 | 1–2 | A | U | A | 0 |
| FILL STD 1 | 0 | 0 | 1 | 0 | 1 | 0 | 0 | 0 | 0 | 1–2 | A | U | A | 0 |
| TRANS WATER STD 1 | 0 | 0 | 0 | 0 | 0 | 0 | 0 | 0 | 1 | 1–2 | B | U | B | 0 |
| FILL STD 2 | 0 | 0 | 0 | 1 | 1 | 0 | 0 | 0 | 0 | 1–2 | B | U | B | 0 |
| TRANS WATER STD 2 | 0 | 0 | 0 | 0 | 0 | 0 | 0 | 0 | 1 | 1–2 | A | U | B | 0 |
| SWEEP TRANS LINE | 1 | 0 | 0 | 0 | 0 | 0 | 0 | 0 | 1 | 1–2 | A | U | C | 0 |
| PREHEAT/ STIR | 0 | 0 | 0 | 0 | 0 | 0 | 0 | 0 | 0 | 1–2 | A | U | A | 0 OR 1 |
| PURGE VIAL | 0 | 1 | 0 | 0 | 0 | 0 | 0 | 0 | 0 | 1–5 4–3 | A | U | C | 0 |
| WAIT FOR DESORB | 0 | 0 | 0 | 0 | 0 | 0 | 0 | 0 | 0 | 1–2 | A | U | C | 0 |
| RINSE LINES | 0 | 0 | 0 | 0 | 0 | 0 | 0 | 1 | 0 | 1–2 | A | U | C | 0 |
| GLASSWR PURGE He | 1 | 0 | 0 | 0 | 0 | 0 | 0 | 0 | 0 | 1–2 | A | U | C | 0 |
| RETURN VIAL TO TRAY | 0 | 0 | 0 | 0 | 0 | 0 | 0 | 0 | 1 | 1–2 | A | D | C | 0 |

Valve L will be directed to permit the flow of helium from valve C through valve P5.

In the syringe fill step, syringe 238 is filled by connecting the water source 232 through valve I and valve P5 in the P5A position to fill the syringe as the plunger is retracted.

selected to permit the operation. It should be noted that when the vial is purged, the valve X5 has ports 1 and 5 and ports 4 and 3 connected so that the volatiles move through the needle for collecting samples and through valve X5 to the line 265 leading to the concentrator for carrying the sample gas.

The line rinse connects the water to valve P5 in its P5C position, and then through valve X6, line 250 and valve X4 to discharge water through line 66 to the sparger fill connection of a sparger or concentrator.

The line purge cycle opens a path through valve C, valve L, valve P5, valve X6, line 250, valve X4, and line 266 to the sparger fill.

A sparger unit 100 that can be mounted onto the front face of the panel includes a U-shaped glass tube 270, that is formed to have a foam trap 272 at one end thereof, and has a neck 274 connected through a purge valve 275 and a flow controller 276 to a source of helium 277. A sample fill connection tube 278 provides for filling material into the interior of the U-shaped glass tube. Connection 278 is connected to the line labeled "to concentrator" in FIGS. 7, 8, or 9. A fitting 279 provided at the top of one leg of the U, opposite from purge valve 275, supports a needle 280 that extends into the sparge tube, a substantial amount. The fitting 279 has a sample outlet to outlet line 282 that leads to a trap module for preparing the sample to be sent to the gas chromatograph. A drain valve 284 also can be provided on the needle head 286 that is attached to the needle 280.

The operation of the sparger module provides for introducing a sample, and for carrying out the sparging function in a preprogrammed manner, controlled by the control circuit 66. Generally there will be a frit in the glass tube 270 just below the end of the needle 280.

The central control unit 66 is a standard programmable unit, such as a microcomputer, that will accept inputs, including the two limit switches for the soil module, two limit switches for the water module indicating the limits of travel for the vial holders, a data entry keyboard, so that particular operations can be keyed in by an operator, inputs for the two switches indicating the vial racks are in position, limit switches for the x and y directions for the transfer arm, the two plungers on the gripper head for indicating position adjacent vial racks, and whether a vial is held in the gripper head. Three potentiometer inputs comprising encoders for the arm movement, including an encoder on the vertical moving drive for the gripper head, and bar code reader input for reading signals from the bar code labels for vial identification in handling are included.

The outputs would include operation of the motor 239, each of the solenoid valves that are shown in FIGS. 7, 8, and 9, the x, y, and z motors for the arm 156 as well as the actuator 200 for the gripper fingers, a motor for the rotating disc 62 at the bar code reader, the magnetic stir motor, and the elevator motors for the soil and water modules, respectively, as well as an output for the heater. All of these outputs can be provided in a desired sequence that can be preprogrammed into the unit, or modified by the data entry keyboard.

Such a programmable unit for the central circuit 66 is well known, and can form any desired type. The operations are sequential, so that the state of various solenoid valves and other operators are changed upon the completion of previous operations in the sequence. The x-y location of the vials in the vial racks can be programmed in, and the positioning of the vial holders for the soil and water module also can be preprogrammed in so that as instructions are given the vial transfer apparatus 28 will go to the proper location.

Modular operation is obtained, with a soil module, a water module or both. The additional valves also can be added with the modules. Valve X5 would be added to the base unit when both modules are used.

The water samples can be waste water or drinking water and rods or sludges can be handled. The bar code reader keeps track of the vials and samples, throughout the test and the controls can insure the results are attached to the proper sample by the bar code use. The bar code reader forms an input to control module 66 and control module can be used to correlate analysis with the appropriate vial. The cooling function for the vials is built into the base unit for convenient and proper test sequencing.

Although the present invention has been described with reference to preferred embodiments, workers skilled in the art will recognize that changes can be made in form and detail without departing from the spirit and scope of the invention.

What is claimed is:

1. A vial autosampler comprising selectable first and second modules, the first module being for sampling liquids and the second module being for obtaining gaseous samples, the modules supporting first and second vials, respectively, each vial being adapted to hold a sample therein;

the vial autosampler further comprising a valve and conduit assembly including a first valve portion comprising a multi port selector valve having a valve block movable to selected positions to connect to ports including a first port connected by a conduit to the first module, and a second port connected through a second valve portion and conduits to the second module, the valve block having a channel that is movable to a position to be filled with a standard to thereby contain the standard; coupleable to the channel and movable to positions to the channel in the valve block being connectable to the first port for permitting a liquid sample to be extracted from the liquid contained in the first vial in the first module and transferred with the standard contained in the channel through the second valve portion to a further analyzation instrument;

the second valve portion being movable to a position to connect the channel to the second module;

a third valve portion comprising a second multi port selector valve coupled to conduits forming portions of both the first and the second modules, and the second multi port selector valve being movable to positions to isolate the second gaseous sample module from the first liquid sample module and coupleable between a source of gas under pressure and a conduit used for the first module in a first isolation position and between the source of gas under pressure and a conduit used for the second module in a second isolation position, the first and second modules being fluidly isolated from each other in both isolation positions of the second multi port selector valve; and the channel connectable to the first port and the liquid module also being connectable through the second valve portion to the second vial in the second module when the second valve portion is moved to a second position, and the second vial being connected to the analyzation instrument with the second multi port valve in its second isolation position.

2. The device of claim 1 wherein the liquid sample module includes a pump for removing a liquid sample from the first vial and passing the liquid sample through the channel in the valve block for mixing a standard therein with the sample, and the pump being operable for injecting a liquid standard from the channel through the second port into a sample in the second vial from which a gaseous sample is obtained.

3. A method of sampling a liquid sample from a first module of an autosampling device, and a gaseous sample from a second module of the autosampling device, comprising the steps of:

providing first and second sampling modules, said modules having first and second sources of samples, respectively;

providing a valve and conduit assembly including a first valve portion comprising a first multi port valve having a valve block movable to selected positions to connect ports including a first port connected by a conduit to the first module, and a second port connected through a second valve portion and conduits to the second module the valve block including a channel that is movable to a position to be filled with a standard;

selectively operating the first multi port selector valve to connect the channel to a standard source and to the first sample source and transfer a first sample and the standard to a remote instrument;

providing a second multi port valve and coupling the second multi port valve to a source of gas under pressure and in a first position the first module and purging portions of the first module while fluidly isolating the second module from the first module;

moving the second multi port valve to a second position when a second sample is to be tested and connecting the source of gas under pressure to the second module, while fluidly isolating the first module from the second module, and to transfer the second sample from the second sample source of the second module to the remote instrument, while maintaining the fluid isolation of the first module from the second module;

moving the channel of the valve block to the position to be filled with the standard; and selectively operating the first multiport selector valve to connect the channel to the standard source and to the second sample source and transfer the second sample and the standard to the remote instrument.

\* \* \* \* \*

UNITED STATES PATENT AND TRADEMARK OFFICE
CERTIFICATE OF CORRECTION

PATENT NO.     : 6,040,186
DATED          : March 21, 2000
INVENTOR(S)    : Lewis et al.

It is certified that error appears in the above-identified patent and that said Letters Patent is hereby corrected as shown below:

<u>Column 18,</u>
Lines 33-34, please delete "coupleable to the channel and movable to position to"

Signed and Sealed this

Fourth Day of November, 2003

JAMES E. ROGAN
*Director of the United States Patent and Trademark Office*